US005508193A

United States Patent [19]
Mandelbaum et al.

[11] Patent Number: 5,508,193
[45] Date of Patent: Apr. 16, 1996

[54] PSEUDOMONAS STRAIN FOR DEGRADATION OF S-TRIAZINES IN SOIL AND WATER

[75] Inventors: Raphael T. Mandelbaum, Rehovot, Israel; Lawrence P. Wackett, St. Paul, Minn.

[73] Assignee: Regents of the University of Minnesota, Minneapolis, Minn.

[21] Appl. No.: 114,695

[22] Filed: Aug. 31, 1993

[51] Int. Cl.$^6$ .................................................. C12N 1/20
[52] U.S. Cl. ............................ 435/253.3; 435/262.5
[58] Field of Search ........................ 435/253.3, 252.1, 435/262, 262.5; 210/601

[56] References Cited

U.S. PATENT DOCUMENTS 4,415,658 11/1983 Cook et al. .
4,915,842 4/1990 Kearney et al. .

OTHER PUBLICATIONS

Ernst et al., Dechema Biotech. Conf., vol. 5, pp. 1101–1104, 1992.
Osman et al., Abstracts of 90th Annual Meeting of ASM, 1990, p. 306.
Environment Today, "Found: Microbes that eat atrazine", *Farm Journal*, 26 (1994).
A. M. Cook et al., "Deethylsimazine: Bacterial Dechlorination, Deamination, and Complete Degradation", *J. Agric. Food Chem.*, 32, 3, 581–585 (1984).
A. M. Cook et al., "s–Triazines as Nitrogen Sources for Bacteria", *J. Agric. Food Chem.*, 29, 6, 1135–1143 (1981).
N. Gschwind, "Biologischer Abbau des Herbizids Atrazin in einem Modellabwasser", *gwf—Wasser/Abwasser*, 134, 65–69 (1993).
P. C. Kearney, "Biodegradation of Ozonated Atrazine as a Wastewater Disposal System", *J. Agric. Food Chem.*, 36, 6, 1301–1306 (1988).
A. Leeson et al., "Biomineralization of Atrazine Ozonation Products. Application to the Development of a Pesticide Waste Disposal System", *J. Agric. Food Chem.*, 41, 6, 983–987 (1993).
C. D. Adams et al., "Ozonation Byproducts of Atrazine in Synthetic and Natural Waters", *Environ. Sci. Technol.*, 26, 2218–2227 (1992).
D. E. Armstrong et al., "Atrazine Hydrolysis in Soil", *Soil Sci. Soc. Am. Proc.*, 31, 61–66 (1967).
D. E. Armstrong et al., "Adsorption Catalyzed Chemical Hydrolysis of Atrazine", *Environ. Sci. Tech.*, 2, 683–689 (1968).
G. Baggi, "Ricerche sulla biodegradabilita di composti triazinici variamente sostituiti", *Ann. Microbiol.*, 31, 13–17 (1981) [English language summary at p. 16].
G. Baggi, "Degradazione microbica delle s–triazine", *Ann. Microbiol.*, 39, 203–212 (1989) [English language summary at p. 210].
R. Behki et al., "Metabolism of the Herbicide Atrazine by Rhodococcus Strains", *Appl. Environ. Microbiol.*, 59, 1955–1959 (1993).

R. M. Behki et al., "Degradation of Atrazine by Pseudomonas: N–Dealkylation and Dehalogenation of Atrazine and Its Metabolites", *J. Agric. Food Chem.*, 34, 746–749 (1986).
J. A. Best et al., "Disappearance of s–Triazines as Affected by Soil pH Using a Balance–Sheet Approach", *Weed Sci.*, 22, 364–373 (1974).
A. M. Cook et al., "Bacterial degradation of N–cyclopropylmelamine, The Steps to Ring Cleavage", *Biochem. J.*, 222, 315–320 (1984).
A. M. Cook et al., "Deethylsimazine: Bacterial Dechlorination, Deamination, and Complete Degradation", *J. Agric. Food Chem.*, 32, 581–585 (1984).
A. M. Cook, "Converging catabolic pathways in the bacterial degradation of s–triazines", *Experientia*, 41, 549 (1985).
A. M. Cook, "Biodegradation of s–triazine xenobiotics", *FEMS Microbiol. Rev.*, 46, 93–116 (1987).
R. W. Couch et al., "The Metabolism of Atrazine and Simazine by Soil Fungi", *Proc. South Weed Sci. Soc.*, 18, 623–631 (1965).
R. W. Eaton et al., "Cloning and Comparison of the DNA Encoding Ammelide Aminohydrolase and Cyanuric Acid Amidohydrolase from three s–Triazine–Degrading Bacterial Strains", *J. Bacter.*, 173, 1363–1366 (1991).
T. A. M. El–Dahtory et al., "Degradation and Utilization of 2,4–dioxohexahydro–1,3,5–triazine (DHT) by Soil Microorganisms", *Zbl. Mikrobiol.* 139, 375–382 (1984) [English language summary at p. 375].
L. E. Erickson et al., "Degradation of Atrazine and Related S–Triazines", *Critical Reviews in Environmental Control*, 19, 1–13 (1989).
C. Fernandez–Quintanilla, "Microbial and Chemical Degradation of Atrazine in Solution", *Proc. EWRS Symp.*, 301–308 (1981).
S. D. Garret, "Isolation and Growth of Fungi in Pure Culture", in *Soil Fungi and Soil Fertility*, Pergamon Press, London, 1981, pp. 76–77.
A. Geller et al., "Studies on the Degradation of Atrazine by Bacterial Communities Enriched from Various Biotopes", *Arch. Environm. Contam. Toxicol.*, 9, 289–305 (1980).
L. P. Gianessi, "Lack of data stymies informed decisions on agricultural pesticides", *Resources*, 89, 1–4 (1987).
M. T. Giardi et al., "Chemical and Biological Degradation of Primary Metabolites of Atrazine by a Nocardia Strain", *Agric. Biol. Chem.*, 49, 1551–1558 (1985).
M. C. Giardina et al., "4–Amino–2–chloro–1,3,5–triazine: A New Metabolite of Atrazine by a Soil Bacterium", *Agric. Biol. Chem.*, 44, 2067–2072 (1980).

(List continued on next page.)

*Primary Examiner*—Irene Marx
*Attorney, Agent, or Firm*—Schwegman, Lundberg, Woessner & Kluth

[57] ABSTRACT

A method for degradation of s-triazine compounds, including atrazine, which utilizes an atrazine degrading Pseudomonas (ADP) bacterium and its enzymes is provided. ADP was isolated from atrazine-contaminated soil and is phylogenetically close to *P. aeruginosa* and *P. citronellolis*. When ADP is cultivated on atrazine medium, it produces enzymes that can completely degrade atrazine to yield $CO_2$ from ring carbons.

1 Claim, 13 Drawing Sheets

OTHER PUBLICATIONS

K. P. Goswami et al., "Microbial Degradation of the Herbicide Atrazine and Its 2–Hydroxy Analog in Submerged Soils", *Environ. Sci. Technol.*, 5, 426–429 (1971).

P. H. H. Gray et al., "Correlation Between Bacterial Numbers and Organic Matter in a Field Soil", *Can. J. Microbiol.*, 3, 711–714 (1957).

H. Gysin et al., "Chemistry and Herbicidal Properties of Triazine Derivatives", in *Advances in Pest Control Research*; R. L. Metcalf, Ed.; Interscience Publishers, Inc.: New York; 1960; pp. 289–358.

R. J. Hance et al., "The Fate of Hydroxyatrazine in a Soil and a Lake Sediment", *Soil Biol. Biochem.*, 1, 309–315 (1969).

C. I. Harris et al., "Fate of 2–Chloro–s–triazine Herbicides in Soil", *J. Agr. Food Chem.*, 15, 157–162 (1967).

J. A. Jessee et al., "Anaerobic Degradation of Cyanuric Acid, Cysteine, and Atrazine by a Facultative Anaerobic Bacterium", *Appl. Environm. Microbiol.*, 45, 97–102 (1983).

D. D. Kaufman et al., "Microbial degradation of s–triazine herbicides", *Residue Rev.*, 32, 235–265 (1970).

D. D. Kaufman et al., "Degradation of Atrazine by Soil Fungi", *Soil Biol. Biochem.*, 2, 73–80 (1970).

W. C. Koskinen et al., "Automation of Atrazine and Alachlor Extraction from Soil Using a Laboratory Robotic System", *Soil Sci. Soc. Am. J.*, 55, 561–562 (1991).

Y. Kruglov, "Herbicide Atrazine Decomposition by Soil Bacteria", *Puchvovedenie*, 7, 112–114 (1983) [English language summary at p. 114].

G. C. Li et al., "Atrazine Hydrolysis as Catalyzed by Humic Acids", *Soil Science*, 114, 201–209 (1972).

R. T. Mandelbaum et al., "Mineralization of the s–Triazine Ring of Atrazine by Stable Bacterial Mixed Cultures", *Appl. Environm. Microbiol.*, 59, 1695–1701 (1993).

R. T. Mandelbaum et al., "Bacterial Degradation of Atrazine—A New Mineralization Pathway", Abstract No. Q–115, 93rd General Meeting of the American Society for Microbiology, Atlanta, Georgia, p. 367 (May 16–20, 1993).

P. B. McMahon et al., "Atrazine Mineralization Potential of Alluvial–Aquifer Sediments under Aerobic Conditions", *Environ. Sci. Technol.*, 26, 1556–1559 (1992).

D. C. Muir et al., "The disappearance and movement of three triazine herbicides and several of their degradation products in soil under field conditions", *Weed Res.*, 18, 111–120 (1978).

D. R. Nair et al., "Effect of Two Electron Acceptors on Atrazine Mineralization Rates in Soil", *Environ. Sci. Technol.*, 26, 2298–2300 (1992).

D. C. Nearpass, "Hydrolysis of Propazine by the Surface Acidity of Organic Matter", *Soil Sci. Soc. Am. Proc.*, 36, 606–610 (1972).

S. R. Obien et al., "Degradation of Atrazine in Four Hawaiian Soils", *Weed Sci.*, 17, 509–514 (1969).

M. Radosevich et al., "Aerobic and Anaerobic Degradation of Atrazine by Surface and Subsurface Microbial Consortia", Abstract No. O–49, 92nd General Meeting of the American Society for Microbiology, New Orleans, Louisiana, p. 317 (1992).

M. Radosevich et al., "The Kinetics of Atrazine Degradation by a Bacterial Isolate in Natural Buried Valley Aquifer Sediments", Abstract No. Q–119, 93rd General Meeting of the American Society for Microbiology, Atlanta, Georgia, p. 367 (May 16–20, 1993).

H. D. Skipper et al., "Microbial Versus Chemical Degradation of Atrazine in Soils", *Soil Sci. Soc. Am. Proc.*, 31, 653–656 (1967).

H. D. Skipper et al., "Biological and Chemical Degradation of Atrazine in Three Oregon Soils", *Weed Science*, 20, 344–347 (1972).

B. A. Sorenson et al., "Formation and Movement of $^{14}C$–Atrazine Degradation Products in a Sandy Loam Soil Under Field Conditions", Ph.D. Thesis, University of Minnesota (1992).

K. Tsuji et al., "16S ribosomal RNA sequence analysis for determination of phylogenetic relationship among methylotrophs", *J. Gen. Microbiol.*, 136, 1–10 (1990).

N. M. J. Vermeulen et al., "Separation of atrazine and some of its degradation products by high–performance liquid chromatography", *J. Chrom.*, 240, 247–253 (1982).

R. M. Viera et al., "Nuevos microorganismos que intervienen en la degradacion de los herbicidas atrazine y simazina", *Ciencias de la Agricultura*, 20/84, 125–126 (1984).

G. Voinova et al., "Detoxication of certain aminotriazine herbicides by soil bacteria", *Medad. Fac. Landbouwwetensch, Rijksuniv. Gent.*, 35, 839–846 (1970) [*Chem. Abs.*, 75, 148, Abstract No. 117414c (1971).

C. R. Woese, "Bacterial Evolution", *Microbiological Reviews*, 51, 221–271 (1987).

D. C. Wolf et al., "Microbial Decomposition of Ring–$^{14}C$ Atrazine, Cyanuric Acid, and 2–Chloro–4,6–diamino–s–triazine", *J. Environ. Qual.*, 4, 134–139 (1975).

L. Xun et al., "Confirmation of Oxidative Dehalogenation of Pentachlorophenol by a Flavobacterium Pentachlorophenol Hydroxylase", *J. Bacteriol.*, 174, 5745–5747 (1992).

R. L. Zimdahl et al., "The Degradation of Triazine and Uracil Herbicides in Soil", *Weed Res.*, 10, 18–26 (1970).

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 1542 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
    ( A ) ORGANISM: Escherichia coli ( x i ) SEQUENCE DESCRIPTION: SEQ ID NO:1:

| | | | | | | |
|---|---|---|---|---|---|---|
| AAAUUGAAGA | GUUUGAUCAU | GGCUCAGAUU | GAACGCUGGC | GGCAGGCCUA | ACACAUGCAA | 60 |
| GUCGAACGGU | AACACGGAAG | AAGCUUGCUU | CUUUGCUGAC | GAGUGGCGGA | CGGGUGAGUA | 120 |
| AUGUCUGGGA | AACUGCCUGA | UGGAGGGGGA | UAACUACUGG | AAACGGUAGC | UAAUACCGCA | 180 |
| UAACGUCGCA | GACCAAAGAG | GGGGACCUUC | GGGCCUCUUG | CCAUCGGAUG | UGCCCAGAUG | 240 |
| GGAUUAGCUA | GUAGGUGGGG | UAACGGCUCA | CCUAGGCGAC | GAUCCCUAGC | UGGUCUGAGA | 300 |
| GGAUGACCAG | CCACACUGGA | ACUGAGACAC | GGUCCAGACU | CCUACGGGAG | GCAGCAGUGG | 360 |
| GGAAUAUUGC | ACAAUGGGCG | CAAGCCUGAU | GCAGCCAUGC | CGCGUGUAUG | AAGAAGGCCU | 420 |
| UCGGGUUGUA | AAGUACUUUC | AGCGGGGAGG | AAGGGAGUAA | AGUUAAUACC | UUUGCUCAUU | 480 |
| GACGUUACCC | GCAGAAGAAG | CACCGGCUAA | CUCCGUGCCA | GCAGCCGCGG | UAAUACGGAG | 540 |
| GGUGCAAGCG | UUAAUCGGAA | UUACUGGGCG | UAAAGCGCAC | GCAGGCGGUU | UGUUAAGUCA | 600 |
| GAUGUGAAAU | CCCCGGGCUC | AACCUGGGAA | CUGCAUCUGA | UACUGGCAAG | CUUGAGUCUC | 660 |
| GUAGAGGGGG | GUAGAAUUCC | AGGUGUAGCG | GUGAAAUGCG | UAGAGAUCUG | GAGGAAUACC | 720 |
| GGUGGCGAAG | GCGGCCCCCU | GGACGAAGAC | UGACGCUCAG | GUGCGAAAGC | GUGGGGAGCA | 780 |
| AACAGGAUUA | GAUACCCUGG | UAGUCCACGC | CGUAAACGAU | GUCGACUUGG | AGGUUGUGCC | 840 |
| CUUGAGGCGU | GGCUUCCGGA | GCUAACGCGU | UAAGUCGACC | GCCUGGGGAG | UACGGCCGCA | 900 |
| AGGUUAAAAC | UCAAAUGAAU | UGACGGGGGC | CCGCACAAGC | GGUGGAGCAU | GUGGUUUAAU | 960 |
| UCGAUGCAAC | GCGAAGAACC | UUACCUGGUC | UUGACAUCCA | CGGAAGUUUU | CAGAGAUGAG | 1020 |
| AAUGUGCCUU | CGGGAACCGU | GAGACAGGUG | CUGCAUGGCU | GUCGUCAGCU | CGUGUUGUGA | 1080 |
| AAUGUUGGGU | UAAGUCCCGC | AACGAGCGCA | ACCCUUAUCC | UUUGUUGCCA | GCGGUCCGGC | 1140 |
| CGGGAACUCA | AAGGAGACUG | CCAGUGAUAA | ACUGGAGGAA | GGUGGGGAUG | ACGUCAAGUC | 1200 |
| AUCAUGGCCC | UUACGACCAG | GGCUACACAC | GUGCUACAAU | GGCGCAUACA | AAGAGAAGCG | 1260 |
| ACCUCGCGAG | AGCAAGCGGA | CCUCAUAAAG | UGCGUCGUAG | UCCGGAUUGG | AGUCUGCAAC | 1320 |
| UCGACUCCAU | GAAGUCGGAA | UCGCUAGUAA | UCGUGGAUCA | GAAUGCCACG | GUGAAUACGU | 1380 |
| UCCCGGGCCU | UGUACACACC | GCCCGUCACA | CCAUGGGAGU | GGGUUGCAAA | AGAAGUAGGU | 1440 |
| AGCUUAACCU | UCGGGAGGGC | GCUUACCACU | UUGUGAUUCA | UGACUGGGGU | GAAGUCGUAA | 1500 |
| CAAGGUAACC | GUAGGGGAAC | CUGCGGUUGG | AUCACCUCCU | UA | | 1542 |

( 2 ) INFORMATION FOR SEQ ID NO:2:

( i ) SEQUENCE CHARACTERISTICS:
        ( A ) LENGTH: 1473 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: Pseudomonas sp. Atrazine-Degrading Isolate
        ( A D P )

( x i ) SEQUENCE DESCRIPTION: SEQ ID NO:2:

| | | | | | | |
|---|---|---|---|---|---|---|
| NUGAAGAGUU | UGAUCAUGGC | UCAGAUUGAA | UUGUGGCGGU | UAGGCCUAAC | ACAUGCAAGU | 60 |
| CGAGCGGAUG | AAGGGAGCUU | GCUUCCCGGA | UUUAGCGGCG | GAUGGGUGAG | UAAUGCCUAG | 120 |

| | | | | | | |
|---|---|---|---|---|---|---|
| GAAUCUGCCU | GGUUAGUGGG | GGACAACGUU | CCGAAAGGAG | CGCUAAUACC | GCAUACGUCC | 180 |
| UCCGGGAGAA | AGUGGGGGAU | CUUCGGACCU | CACGCUAUCC | SAUGAGCCUA | GGGCGGAUUA | 240 |
| GCUAGUAGGU | GGGGUAAUGG | CUCACCUAGG | CGACGAUCCG | UAACUGGUCU | GAGAGGAUGA | 300 |
| UCAGUCACAC | UGGAACUGAG | ACACGGUCCA | GUCUCCUACG | GGAGGCAGCA | GUGGGGAAUA | 360 |
| UUGGACAAUG | GGCGAAAGCC | UNAUCCAGCC | AUGCCGCGUG | UGUGAAGAAG | GUCUUCGGAU | 420 |
| UGUAAAGCAC | UUUAAGUUGG | GAGGAAGGGC | AGUAAGUUAA | UACCUUGCUN | UUUUGACGUU | 480 |
| ACCAACAGAA | UAAGCACCGG | CUAACUUCGU | GCCAGCAGCC | GCGGUAAUAC | UGAAGGGUGC | 540 |
| UAGCGUUAAU | CGGAAUUACU | GGGYGUAAAG | CGCGCGUAGG | UGGUUUGGUA | AGAUGGAUGU | 600 |
| GAAAUCCCCG | GGCUCAACCU | GGGGACUGCA | UCCAUAACAU | CCUGACUAGA | GGACGGUAGA | 660 |
| GGGUGGUGGA | AUUUCCUGUG | UAGCGGUGAA | AUGCGUAGAU | AUAGGAAGGA | ACACCAGUGG | 720 |
| CGAAGGCGAC | CACCUCGACU | GAUACUGACC | CUGAGGUGCG | CAAGCUGGGG | AGCMAACAGG | 780 |
| AUUAGAUACC | CUGGUAGUCC | ACGCCGUCAA | CGAUGUCGAC | UAGCCGÜUGG | GAUCCUUGAG | 840 |
| AUCUUAGUGG | CGCAGUAAGG | CGAUAAGUCG | ACCGCCUGGG | GCGUACGGCC | GCAAGGUUAA | 900 |
| AACUCAAAUG | AUUCAGGGGG | CCGCACAACC | GGUGGAGCAU | GUGGUUUAAU | UCGAANNAAC | 960 |
| GCGAAGAACC | UUACCUGGCC | UUGACAUGUC | CGGAAUCYUG | CAGAGCAUGC | GAGAGYCCUU | 1020 |
| CGGGAAUCGG | AACACAGGUG | CUGCAUGGCU | GUCGUCAGGH | UCAGUGGUCG | UGAGAUGUUG | 1080 |
| GGUUAAGUCC | CGUAACGAGC | GCAACCCUUG | UCCUUAGUUA | CCAGCACGUU | CAGGUGGGCA | 1140 |
| CUCUAAGGAG | ACUGCCGGUG | ACAAACGGA | CGGAAGGUGG | GGAUGACGUC | AAGUCAUCAU | 1200 |
| GGCCCUUACG | GCCAGGGCUA | CACACGUGCU | ACAAUGGUCG | GUACAGAGGG | UUGCCAAGCC | 1260 |
| GCGAGGUGGA | GCUAAUCCCA | GAAAACCGAU | CGUAGUCCGG | AUCGCAGUCU | GCAACUCGAC | 1320 |
| UGCGUGAAGU | CGGAAUCGCU | AGUAAUCGUG | AAUCAGAAUG | UCACGGUGAA | UACGUUCCCG | 1380 |
| GGCCUUGUAC | ACACCGCCCG | UCACACCAUG | GGAGUGGGUU | GCUCCAGAAG | UAGCUAGUCU | 1440 |
| AACCGCAAGG | GGGACGGUUA | CCACGGAGUG | AUU | | | 1473 |

( 2 ) INFORMATION FOR SEQ ID NO:3:

( i ) SEQUENCE CHARACTERISTICS:
        ( A ) LENGTH: 386 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: Pseudomonas citronellolis ( x i ) SEQUENCE DESCRIPTION: SEQ ID NO:3:

| | | | | | | |
|---|---|---|---|---|---|---|
| GGAHUCUGCC | UBGUAGUGGG | GGACAACGUU | CCGAAAYGAG | CGCUAAUACC | GCAUACGUCC | 60 |
| UACGGGAGAA | AGUGGGGGAU | CUUCGGACCU | CACGCUAUGA | NAUGAGCCUA | GGUCGGAUUA | 120 |
| GCUAGUAGGU | GGGGUAAUGG | CUCACCUAGG | CGACGAUCCG | NAACURGUCU | GAGAGGAUGA | 180 |
| UCAGUCACAC | UGGAACUGAG | ACACGGUCCA | GYCUCCUACG | GGHGGCAGCA | GUGGGHAUA | 240 |
| UUGGACAAUG | GGCGAAAGCC | YBAUCCAGCC | AUGCCGCGUG | UGUGAAGAAG | GUCUUCGGAU | 300 |
| UGUAAAGCAC | UUUAAGUUGG | GAGGAAGGGC | AGUAAGUUAA | UACCUUGCUN | UUUUGACGUU | 360 |
| ACCAACAGAA | UAAGCACCGG | CUAACU | | | | 386 |

( 2 ) INFORMATION FOR SEQ ID NO:4:

( i ) SEQUENCE CHARACTERISTICS:
    ( A ) LENGTH: 153 base pairs
    ( B ) TYPE: nucleic acid
    ( C ) STRANDEDNESS: single
    ( D ) TOPOLOGY: linear ( i i ) MOLECULE TYPE: rRNA ( v i ) ORIGINAL SOURCE:
    ( A ) ORGANISM: Pseudomonas citronellolis ( x i ) SEQUENCE DESCRIPTION: SEQ ID NO:4:

| | | | | | | |
|---|---|---|---|---|---|---|
| GUAAUACGAA | UGGUGCUAAG | CGUUAAUUCG | GAAUUACUGG | GYGUAAAGCG | CGCGUAGGUK | 60 |
| UUUGGUAAGA | UGGAUGUGAA | AUAAAGGGC | UCAACCUGGU | WACUGCAUCC | AUAACUGCCU | 120 |
| GACUAGAGUA | CGUGUAUAGG | GUGGURGAAU | UUC | | | 153 |

( 2 ) INFORMATION FOR SEQ ID NO:5:

( i ) SEQUENCE CHARACTERISTICS:
    ( A ) LENGTH: 660 base pairs
    ( B ) TYPE: nucleic acid
    ( C ) STRANDEDNESS: single
    ( D ) TOPOLOGY: linear ( i i ) MOLECULE TYPE: rRNA ( v i ) ORIGINAL SOURCE:
    ( A ) ORGANISM: Pseudomonas citronellolis ( x i ) SEQUENCE DESCRIPTION: SEQ ID NO:5:

| | | | | | | |
|---|---|---|---|---|---|---|
| AAGGCGACCA | CCUGACUGAU | ACUGACACUG | AGGUGCGHAA | GCGUGGGGAG | CAAACAGGAU | 60 |
| UAGAUACCCU | GGUAGUCCAC | GCCGUAAACG | AUGUCGACUA | GCCGUUGGGA | UCUUGAGAUC | 120 |
| UUAGUAGGCG | CACGUAACGC | GAUAAGUCGA | CCGCCUGGGG | AGUACGGCCG | CAAGGUUAAA | 180 |
| ACUCAAAUGC | AUUUACGGGG | GCCGCACAAG | CGGUGGAGCA | UGUGGUUUAA | UUCGAANNAA | 240 |
| CGCGAAGAAC | CUUACCUGGC | CUUGACAUGU | CCGGAAUUCU | GUAGAGYAUG | CGGGAGUGCC | 300 |
| UUCGGGAAUC | GGAACACAGG | UGCUGCAUGG | CUGUCGUCAG | CUCAGUGGUC | GUGAGAUGUN | 360 |
| GGGUUAAGUC | CCGUAACGAG | CGCAACCCUU | GUCCUUAGUU | ACCAGCACGU | UAUGGUGGGC | 420 |
| ACUCUAAGGA | GACUGCCGGU | GACUAAACCG | GAGGCAGGYG | GGAUGACGU | CAAGUCAUCA | 480 |
| UCCUUACGGC | YAGGGCUACA | CACGUGCUAC | AAUGGUCGGU | ACAGACGGGU | UGCCCAAGCC | 540 |
| GAGAGGUCGA | SCUAAUCCCA | GAAAACCGAU | CGUAGUCCGG | AUCGCAGUCU | GCAACUCGAC | 600 |
| UGCGUGAAGU | CGGAAUCGCU | AGUAAUCGUG | UGAAUCAGAA | UGUCACGGUG | AAUACGUUCC | 660 |

( 2 ) INFORMATION FOR SEQ ID NO:6:

( i ) SEQUENCE CHARACTERISTICS:
    ( A ) LENGTH: 1518 base pairs
    ( B ) TYPE: nucleic acid
    ( C ) STRANDEDNESS: single
    ( D ) TOPOLOGY: linear ( i i ) MOLECULE TYPE: rRNA ( v i ) ORIGINAL SOURCE:
    ( A ) ORGANISM: Pseudomonas aeruginosa ( x i ) SEQUENCE DESCRIPTION: SEQ ID NO:6:

| | | | | | | |
|---|---|---|---|---|---|---|
| AUACUGAAGA | GUUUGAUCAU | GGCUCAGAUU | GAACGCUGGC | GGCAGNGCCU | AACACAUGCA | 60 |
| AGUCGAGCGG | AUGAAGGGAG | CUUGCUCCUG | GAUUCAGCGG | CGGACGGGUG | AGUAAUGCCU | 120 |
| AGGAAUCUGC | CUGAUAGUGG | GGGAUAACGU | CCGGAAACGG | GCGCUAAUAC | CGCAUACGUC | 180 |
| CUGAGGGAGA | AAGGGGGGGA | UCCUCGGACC | UCACGCUAUC | NGAUGAGCCU | AGGUCGGAUU | 240 |

| | | | | | | |
|---|---|---|---|---|---|---|
|AGCUAGUUGG|UGGGGUAAAG|GCCUACCAAG|GCGACGAUCC|GUAACUGGUC|UGAGAGGACG|300|
|AUCAGUCACA|CUGGAACUGA|GACACGGUCC|AGACUCCUAC|GGGAGGCAGC|AGUGGGGAAU|360|
|AUUGGACAAU|GGGCGAAAGC|CNGAUCCAGC|CAUGCCGCGU|GUGUGAAGAA|GGUCUUCGGA|420|
|UUGUAAAGCA|CUUUAAGUUG|GGAGGAAGGG|CAGUAAGUUA|AUACCUUGCU|GUUUUGACGU|480|
|UACCAACAGA|AUAAGCACCG|GCUAACUUCG|UGCCAGCAGC|CGCGGUAAUA|CGAAGGGUGC|540|
|GAGCGUUAAU|CGGAAUUACU|GGGCGUAAAG|CGCGCGUAGG|UGGUUCAGCA|AGUUGGAUGU|600|
|GAAAUCCCCG|GGCUCAACCU|GGGAACUGCA|UCCNAAACUA|CUGAGCUAGA|GUACGGUAGA|660|
|GGGUGGUGGA|AUUUCCUGUG|UAGCGGUGAA|AUGCGUAGAU|AUAGGAAGGA|ACACCAGUGG|720|
|CGAAGGCGAC|CACCUGGACU|GAUACUGACA|CUGAGGUGCG|AAAGCGUGGG|GAGCAAACAG|780|
|GAUUAGAUAC|CCUGGUAGUC|CACGCCGUAA|ACGAUGUCGA|CUAGCCGUUG|GGAUCCUUGA|840|
|GAUCUUAGUG|GCGCAGCUAA|CGCGAUAAGU|CGACCGCCUG|GGGAGUACGG|CCGCAAGGUU|900|
|AAAACUCAAA|UGAAUUGACG|GGGGCNNGCA|CAAGCGGUGG|AGCAUGUGGU|UUAAUUCGAA|960|
|GCAACGCGAA|GAACCUUACC|UGGCCUUGAC|AUGCUGAGAA|CUUUCCAGAG|AUGGAUUGGU|1020|
|GCCUUCGGGA|ACUCAGACAC|AGGUGCUGCA|UGGCUGUCGU|CAGCUCGUGU|CGUGAGAUGU|1080|
|UGGGUUAAGU|CCCGUAACGA|GCGCAACCCU|UGUCCUUAGU|UACCAGCACC|UCGGGUGGGC|1140|
|ACUCUAAGGA|GACUGCCGGU|GACAAACCGG|AGGAAGGUGG|GGAUGACGUC|AAGUCAUCAU|1200|
|GGCCCUUACG|GCNAGGGCUA|CACACGUGCU|ACAAUGGUCG|GUACAAAGGG|UUGCGAAGCC|1260|
|GCGAGGUGGA|GCUAAUCCCA|UAAAACCGAU|CGUAGUCCGG|AUCGCAGUCU|GCAACUCGAC|1320|
|UGCGUGAAGU|CGGAAUCGCU|AGUAAUCGUG|AAUCAGAAUG|UCACGGUGAA|UACGUUCCCG|1380|
|GGCCUUGUAC|ACACCGCCCG|UCACACCAUG|GGAGUGGGUU|GCUCCAGAAG|UAGCUAGUCU|1440|
|AACCGCAAGG|GGGACGGUUA|CCACGGAGUG|AUUCAUGNNN|NNNNNNNNN|NGUAACAAGN|1500|
|NNNNNNNNN|NGAACCUG| | | | |1518|

( 2 ) INFORMATION FOR SEQ ID NO:7:

( i ) SEQUENCE CHARACTERISTICS:
        ( A ) LENGTH: 1536 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: Pseudomonas testosteroni ( x i ) SEQUENCE DESCRIPTION: SEQ ID NO:7:

| | | | | | | |
|---|---|---|---|---|---|---|
|GAACUAUAGA|GUUUGAUCCU|GGCUCAGAUU|GAACGCUGGC|GGCAUGCUU|UACACAUGCA|60|
|AGUCGAACGG|UAACAGGUCU|UCGGAUGCUG|ACGAGUGGCG|AACGGGUGAG|UAAUACAUCG|120|
|GAACGUGCCU|AGUAGUGGGG|GAUAACUACU|CGAAAGAGUA|GCUAAUACCG|CAUGAGAUCU|180|
|ACGGAUGAAA|GCAGGGGACC|UUCGGGCCUU|GUGCUACUAG|AGCGGCUGAU|GGCAGAUUAG|240|
|GUAGUUGGUG|GGGUAAAGGC|UUACCAAGCC|UGCGAUCUGU|AGCUGGUCUG|AGAGGACGAC|300|
|CAGCCACACU|GGGACUGAGA|CACGGCCCAG|ACUCCUACGG|GAGGCAGCAG|UGGGGAAUUU|360|
|UGGACAAUGG|GCGAAAGCCU|GAUCCAGCAA|UGCCGCGUGC|AGGAUGAAGG|CCCUCGGGUU|420|
|GUAAACUGCU|UUUGUACGGA|ACGAAAAGCC|UGGGGCUAAU|AUCCCGGGU|CAUGACGGUA|480|
|CCGUAAGAAU|AAGCACCGGC|UAACUACGUG|CCAGCAGCCG|CGGUAAUACG|UAGGGUGCAA|540|
|GCGUUAAUCG|GAAUUACUGG|GCGUAAAGCG|UGCGCAGGCG|GUUUGUAAG|ACAGUGGUGA|600|

| | | | | | | |
|---|---|---|---|---|---|---|
|AAUCCCCGGG|CUCAACCUGG|GAACUGCCAU|UGUGACUGCA|AGGCUAGAGU|GCGGCAGAGG|660|
|GGGAUGGAAU|UCCGCGUGUA|GCAGUGAAAU|GCGUAGAUAU|GCGGAGGAAC|ACCGAUGGCG|720|
|AAGGCAAUCC|CCUGGGCCUG|CACUGACGCU|CAUGCACGAA|AGCGUGGGGA|GCAAACAGGA|780|
|UUAGAUACCC|UGGUAGUCCA|CGCCCUAAAC|GAUGUCAACU|GGUUGUUGGG|UCUUAACUGA|840|
|CUCAGUAACG|AAGCUAACGC|GUGAAGUUGA|CCGCCUGGGG|AGUACGGCCG|CAAGGUUGAA|900|
|ACUCAAAGGA|AUUGACGGGG|ACCCGCACAA|GCGGUGGAUG|AUGUGGUUUA|AUUCGAUGCA|960|
|ACGCGAAAAA|CCUUACCCAC|CUUUGACAUG|GCAGGAACUU|ACCAGAGAUG|GUUUGGUGCU|1020|
|CGAAAGAGAA|CCUGCACACA|GGUGCUGCAU|GGCUGUCGUC|AGCUCGUGUC|GUGAGAUGUU|1080|
|GGGUUAAGUC|CCGCAACGAG|CGCAACCCUU|GCCAUUAGUU|GCUACAUUCA|GUUGAGCACU|1140|
|CUAAUGGGAC|UGCCGGUGAC|AAACCGGAGG|AAGGUGGGGA|UGACGUCAAG|UCCUCAUGGC|1200|
|CCUUAUAGGU|GGGGCUACAC|ACGUCAUACA|AUGGCUGGUA|CAAAGGGUUG|CCAACCCGCG|1260|
|AGGGGGAGCU|AAUCCCAUAA|AGCCAGUCGU|AGUCCGGAUC|GCAGUCUGCA|ACUCGACUGC|1320|
|GUGAAGUCGG|AAUCGCUAGU|AAUCGUGGAU|CAGAAUGUCA|CGGUGAAUAC|GUUCCCGGGU|1380|
|CUUGUACACA|CCGCCCGUCA|CACCAUGGGA|GCGGGUCUCG|CCAGAAGUAG|GUAGCCUAAC|1440|
|CGUAAGGAGG|GCGCUUACCA|CGGCGGGGUU|CGUGACUGGG|GUGAAGUCGU|AACAAGGUAG|1500|
|CCGUAUCGGA|AGGUGCGGCU|GGAUCACCUC|CUUUCU| | |1536|

( 2 ) INFORMATION FOR SEQ ID NO:8:

( i ) SEQUENCE CHARACTERISTICS:
        ( A ) LENGTH: 1474 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: Pseudomonas cepacia ( x i ) SEQUENCE DESCRIPTION: SEQ ID NO:8:

| | | | | | | |
|---|---|---|---|---|---|---|
|NNACUGAAGA|GUUUNAUCCU|GGCUCAGAUU|NAACGCUGGC|GGCAUGCCUU|ACACAUGCAA|60|
|GUCGAACGGC|NAGCAUCGGG|UGCUUNCACC|UGUGGCGAGU|GGCGAACGGG|UGAGUAAUAC|120|
|AUCGGAACAU|GUCCUGUAGU|GGGGGAUAGC|NCGGCGAAAG|CCNNAUUAAU|ACCGCAUACG|180|
|AUCUACGGAU|GAAAGCGGGN|GACCUUCGGG|CCUCGCGCUA|UAGGGUUGGC|CGAUGGCUGA|240|
|UUAGCUAGUU|GGUGGGGUAA|AGGCCUACCA|AGGCGACGAU|CAGUAGCUNG|UCUGAGAGGA|300|
|CGACCAGCCA|CACUGGGACU|GAGACACGGC|CCNGACUCCU|ACGGGAGGCA|GCAGUGGGA|360|
|AUUUUGGACA|AUGGGCGAAA|GCCUGAUCCA|GCAAUGCCGC|GUGUGUGAAG|AAGGCCUUCG|420|
|GGUUGUAAAG|CACUUUUGUC|CGGAAGAAA|UCCUUGGCUC|UAAUACAGCC|GGGGGAUGAC|480|
|GGUACCGGAA|GAAUAAGCAC|CGGCUAACUA|CGUGCNAGCA|GCCGCGNNNA|UACGUAGGGU|540|
|GCAAGCGUUA|AUCGGAAUUA|CUGGGCGUAA|AGCGUGCGCA|GGCGGUUUGC|UAAGACCGAU|600|
|GUGAAAUCCC|CGGGCUCAAC|CUGGGNACUG|CAUUGGUGAC|UGGCAGGCUA|GAGUAUGNNA|660|
|GAGGGGGGUA|GAAUUCCACG|UGUAGCAGUG|AAAUGCGUAG|AGAUGUGGAG|GAAUACCGAU|720|
|GGCGAAGGCA|GCCCCUGGG|CCAAUACUGA|CGCUCAUGCA|CGAAAGCGUG|GGGAGCAAAC|780|
|AGGAUUAGAU|ACCCUGGUAG|UCCACGCCCU|AAACGAUGUC|AACUAGUUGU|UGGGGAUUCA|840|
|UUUCCUUAGU|AACGUAGCUA|ACGCGUGAAG|UUGACCGCCU|GGGGAGUACG|GUCGCAAGAU|900|
|UAAAACUCAA|AGGAAUUGAC|GGGGACCCGC|ACAAGCGGUG|GAUGAUGUGG|AUUAAUUCGA|960|

| | | | | | | |
|---|---|---|---|---|---|---|
| UGNAACGCGA | AAAACCUUAC | CUACCCUUGA | CAUGGUCGGA | AUCCUGCUGA | GAGGCGGGAG | 1020 |
| UGCUCGAAAG | AGAACCGGCG | CACAGGUGCU | GCAUGGCUGU | CGUCAGCUCG | UGUCGUGAGA | 1080 |
| UGUUGGGUUA | AGUCCCGCAA | CGAGCGCAAC | CCUUGUCCUU | AGUUGCUACG | CNAGAGCACU | 1140 |
| CUAAGGAGAC | UGCCGGUGAC | AAACCGGAGG | AAGGUNGGGA | UGACGUCAAG | UCCUCAUGGC | 1200 |
| CCUUAUGGGU | AGGGCUUCAC | ACGUCAUACA | AUGGUCGGAA | CAGAGGGUUG | CCAACCCGCG | 1260 |
| AGGGGAGCU | AAUCCCAGAA | AACCGAUCGU | AGUCCGGAUU | GCACUCUGCA | ACUCGAGUGC | 1320 |
| AUGAAGCUGG | AAUCGCUAGU | AAUCGCGGAU | CAGCAUGCCG | CGGUGAAUAC | GUUCCCGGGU | 1380 |
| CUUGUACACA | CNGCCCGUCA | CACCAUGGGA | GUGGGUUUUA | CCAGAAGUGG | CUAGUCUAAC | 1440 |
| CACAAGGAGG | ANNGUCACNA | NGGUAGGAUU | NANG | | | 1474 |

PSEUDOMONAS STRAIN FOR DEGRADATION OF S-TRIAZINES IN SOIL AND WATER

FIELD OF THE INVENTION

The present invention relates to methods of biologically degrading s-triazine compounds, particularly chlorinated s-triazine compounds, including atrazine.

BACKGROUND OF THE INVENTION

Atrazine (2-chloro-4-ethylamino-6-isopropylamino-1,3,5-triazine) is a widely used s-triazine (i.e., symmetric triazine) herbicide. Approximately 800 million pounds were used in the United States between 1980 and 1990. Numerous studies on the environmental fate of atrazine have shown that atrazine is a recalcitrant compound that is transformed to $CO_2$ very slowly, if at all, under aerobic or anaerobic conditions. It has a water solubility of 33 mg/L at 27° C. Its half-life, i.e., time required for half of the original concentration to dissipate, can vary from about 4 weeks to 57 weeks if in soils at low concentration, i.e., less than about 2 parts per million (ppm). High concentrations of atrazine, such as those occurring in spill sites have been reported to dissipate even more slowly.

As a result of its widespread use, atrazine is often detected in ground water and soils in concentrations exceeding the maximum contaminant level (MCL) of 3 µg/L, i.e., 3 parts per billion (ppb), a regulatory level that took effect in 1992. Point source spills of atrazine have resulted in levels as high as 25 ppb in some wells. Levels of up to 40,000 mg/L, i.e., 40,000 parts per million (ppm) atrazine have been found in the soil of spill sites more than ten years after the spill incident. Such point source spills and subsequent runoff can cause crop damage and ground water contamination.

Current technology for reclaiming soil polluted with s-triazine compounds involves incineration or land farming of the polluted soil. Decontamination of ground-water containing s-triazine compounds involves pumping water to the surface and removing the pollutants on a sorbent. Similar technology is currently used for the decontamination of waste water from atrazine manufacturing plants. These are expensive methods and/or produce concentrated toxic materials that may present future hazards.

The persistence of atrazine in the environment has stimulated investigations into its biodegradation using bacterial cultures. The results have been of limited success, however. See, for example, Geller, *Arch. Environ. Contam. and Toxicol.*, 9, 289–305 (1980); and Fernandez-Quintanilla et al., *Proc. EWRS Symp.*, 301–308 (1981). Generally, less heavily substituted and nonchlorinated s-triazines are more biodegradable than is atrazine. For example, two soil fungi have been shown to degrade cyanuric acid, a nonchlorinated s-triazine, but not atrazine, to $CO_2$. See, Wolf and Martin, *J. Environ. Qual.*, 4, 134–139 (1975).

Certain bacteria (Pseudomonas and Klebsiella) have been isolated that are capable of utilizing specific s-triazine compounds, but not atrazine, as a sole nitrogen source. See, for example, Cook, *FEMS Microbiol. Letters*, 46, 93–116 (1987). Other Pseudomonas strains N-dealkylate atrazine and use the side chain carbons for supporting slow growth, but they do not degrade the s-triazine ring. See, for example, Behiki and Khan, *J. Agric. Food Chem.*, 34, 746–749 (1986), and McMahon et al., *Environ. Sci. Technol.*, 26, 1556–1559 (1992).

Other bacteria have been isolated that can degrade the ethyl or isopropyl side chains of atrazine; however, only N-dealkylation of the atrazine side chains typically occurs. Complete and rapid metabolism of the s-triazine ring or dechlorination has been demonstrated in very few situations. For example, a Nocardia sp. strain is capable of dealkylating and deaminating atrazine to form the unstable metabolite 4-amino-2-chloro-1,3,5-triazine, which is reported to undergo rapid chemical dechlorination followed by spontaneous ring cleavage. See, Giardi et al., *Agric. Biol. Biochem.*, 49, 1551–1558 (1985). Recently, a very slow liberation of $CO_2$ from the atrazine ring was observed in soil bioreactors. See, Nair et al., *Environ. Sci. Technol.*, 26, 2298–2300 (1992). Less than 10% of uniform ring labeled [$^{14}C$]atrazine was converted to $^{14}CO_2$ in 125 days.

Besides bacteria, the low specific activity of some enzymes involved in the degradation of atrazine metabolites from known microorganisms has proven to be too low for practical use in the degradation of s-triazine waste. See, for example, Cook, *FEMS Microbiol. Rev.*, 46, 93–116 (1987). In sum, most known organisms exhibit slow rates of atrazine dealkylation and do not efficiently dechlorinate atrazine or destroy the s-triazine ring.

Thus, the use of microorganisms to completely degrade atrazine and less bulky s-triazine compounds is to date not commercially viable. However, no one has fully exploited the atrazine degradation ability of bacteria, nor in particular the enzymes of such bacteria, in order to both rapidly and completely degrade atrazine and related s-triazine compounds. Accordingly, there is a need for a method to rapidly and completely degrade atrazine and related s-triazine compounds by employing bacterial cells or by employing cell-free preparations from such bacteria induced to produce enzymes involved in the degradation process.

SUMMARY OF THE INVENTION

The present invention provides a biologically pure culture of a strain of the genus Pseudomonas that is tolerant of high atrazine concentrations, and preferably also of high concentrations of other s-triazine compounds. It is capable of detoxifying, i.e., degrading atrazine substantially completely such that there are substantially no toxic intermediates formed. This is a result of degradation of the s-triazine ring and mineralization of all possible organic intermediates to inorganic compounds and ions, e.g., $CO_2$. The bacteria is referred to herein as an atrazine degrading Pseudomonas (ADP) bacteria, i.e., a strain of bacteria capable of degrading atrazine.

The strain exhibits sustained growth in media containing atrazine as the sole nitrogen source, and preferably sodium citrate as the sole carbon source. Preferably, this bacterial strain exhibits substantially constant growth, i.e., sustained growth, at atrazine solution concentrations of at least about 100 mg/L (ppm) and at a temperature of about 20°–40° C. It also exhibits sustained growth under oxygen limited conditions. Furthermore, the bacterial strain of the present invention detoxifies s-triazine compounds in water or solid samples, such as soil, that contain the s-triazine compound in a wide variety of concentrations, e.g., at the ppb level up to the thousands of ppm level and higher. The isolation and characterization of these bacteria and their use in methods of detoxifying s-triazine-contaminated materials by microbial degradation are described.

The methods of the present invention for degrading s-triazine compounds particularly atrazine, are advantageous because they rapidly and substantially completely degrade the compounds using a single bacterium species. Specifically, the methods of the present invention involve the reaction of a growing Pseudomonas bacterium, a non-growing Pseudomonas bacterium, or a cell-free preparation of a Pseudomonas bacterium with a sample containing atrazine or other s-triazine compounds. The sample can be a sample of a solid material such as soil, water, or waste-water, for example. The bacterium of the present invention is particularly useful because it is capable of degrading high concentrations of aged atrazine in native soils, which is very difficult to degrade because aged herbicides tend to be bound to soil. As used herein, "aged" atrazine refers to atrazine present in soils for a period greater than one year.

More specifically, a method of degrading an s-triazine compound involves contacting a sample containing therein a dissolved s-triazine compound with an atrazine-degrading bacterium; wherein the bacterium is a member of the genus Pseudomonas, is capable of sustained growth in media comprising atrazine as the sole nitrogen source, and is capable of degrading the triazine ring of the s-triazine compound. Preferably, the sample is contacted with an amount of the atrazine-degrading bacterium effective to degrade the s-triazine compound at a rate of 10 mmoles per hour per gram cell protein. More preferably, the sample is contacted with an aqueous medium containing about 0.1–20 g/L of the atrazine-degrading bacterium. To provide more effective degradation, the atrazine-degrading bacterium is first subjected to a culture to stimulate atrazine-degrading enzymes.

The method of the present invention can utilize growing cells of the ADP bacterium, nongrowing cells of the ADP bacterium, or a cell extract containing enzymes generated by the ADP bacterium. The method of the present invention can also use the ADP bacterium in a biologically pure culture or in a mixed culture. As used herein, a "mixed" culture is one containing an assemblage of organisms including the ADP bacterium of the present invention.

DETAILED DESCRIPTION OF THE INVENTION

Figure 1:
FIG. 1: Transmission Electron Microscope (TEM) picture of an atrazine degrading Pseudornonas (ADP). The bacterium was isolated from a 48-hour old liquid culture growing in an atrazine medium. The bacterium was negatively stained with uranyl acetate. The magnification is 25,060x.

The present invention provides a pure strain of an atrazine degrading Pseudomonas (ADP), i.e., a bacterium capable of degrading atrazine, and preferably other s-triazine compounds. The present invention also provides methods of rapidly and completely degrading atrazine and other herbicides of the s-triazine family. Such compounds have the general formula (Formula I):

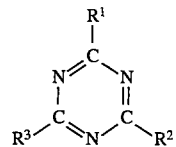

Of the s-triazine compounds of Formula I, the most widely used is atrazine. It is primarily used as a selective pre- or post-emergence herbicide in corn and sorghum and a variety of other crops. Atrazine (2-chloro-4-ethylamino-6-isopropylamino-1,3,5-triazine) is an aromatic halogenated s-triazine ring with an amino-ethyl and aminoisopropyl side chains and a chlorinated ring carbon, i.e., it has the structure of Formula I wherein $R^1$=Cl, $R^2$=NH—$C_2H_5$, and $R^3$=NH—i—$C_3H_7$.

Other s-triazine compounds that can be degraded by the bacterium of the present invention include, for example: simazine ($R^1$=Cl, $R^2$ and $R^3$=NH—$C_2H_5$; 2-chloro-4,6-bis-(ethylamino)-1,3,5-triazine); desisopropylatrazine ($R^1$=Cl, $R^2$=$NH_2$, $R^3$=NH—$C_2H_5$; 2-chloro-4-ethylamino- 6-amino-1,3,5-triazine); desethylatrazine ($R^1$= Cl, $R^2$=$NH_2$, $R^3$=NH—i—$C_3H_7$; 2-chloro-4-amino-6-isopropylamino-1,3,5-triazine); hydroxyatrazine ($R^1$=OH, $R^2$=NH—$C_2H_5$, and $R^3$=NH—i—$C_3H_7$; 2-hydroxy-4-ethylamino-6-isopropylamino-1,3,5-triazine); desethyldesisopropylatrazine ($R^1$=Cl, $R^2$=$NH_2$, $R^3$=$NH_2$; chloro-diamino-1,3,5-triazine); desethylhydroxyatrazine ($R^1$=OH, $R^2$=$NH_2$, and $R^3$=NH—i—$C_3H_7$; 2-hydroxy-4-amino-6-isopropylamino-1,3,5-triazine); cyanuric acid ($R^1$=OH, $R^2$=OH, $R^3$=OH; 2,4,6-trihydroxy-1,3,5-atrazine); propazine ($R^1$=Cl, $R^2$=NH—i—$C_3H_7$, and $R^3$=NH—i—$C_3H_7$; 2-chloro-4,6-bis(isopropylamino)-1,3,5-triazine); cyanazine ($R^1$=Cl, $R^2$=NH—$C_2H_5$, and $R^3$=NH—$C_3H_6$(CN); 2-[(4-chloro-6-ethylamino-1,3,5-triazine-2-yl)amino]-2-methyl propionitrile); desethylcyanazine ($R^1$=Cl, $R^2$=$NH_2$, and $R^3$=NH—$C_3H_6$(CN); 2-[(4-chloro-6-amino-1,3,5-triazine-2-yl)amino]-2-methyl propionitrile); melamine ($R^1$=$NH_2$, $R^2$=$NH_2$, $R^3$=$NH_2$; 2,4,6-triamino-1,3,5-atrazine); desisopropylhydroxyatrazine ($R^1$=OH, $R^2$=NH—$C_2H_5$, $R^3$=$NH_2$; 2-hydroxy-4-ethylamino-6-amino-1,3,5-atrazine); ammeline ($R^1$=OH, $R^2$=$NH_2$, $R^3$=$NH_2$; 2-hydroxy-4,6-diamino-1,3,5-atrazine); and others.

The methods of the present invention utilize an atrazine degrading Pseudomonas (ADP) bacterium to degrade atrazine and other s-triazines. Until this invention, no other Pseudomonas species, nor any other bacterium, has been reported to degrade atrazine as rapidly or as completely. For example, no other bacterium can degrade atrazine at initial concentrations of up to about 2000 ppm in minutes or hours such that the triazine ring is substantially completely degraded, i.e., substantially stoichiometrically transformed to $CO_2$.

ADP Bacterium

The ADP bacterium of the present invention is member of the genus Pseudomonas having the characteristics as set forth in Table 1 below.

TABLE 1

| Characteristics of the ADP Bacterium | | |
|---|---|---|
| Morphology: | Rod-shaped motile bacterium, with a polar flagellum (FIG. 1). This flagellum is often lost resulting in what appears to be a flagellum-less gram negative rod. Length = approximately 2 μm. No sheath or prosthecae. | |
| Gram Stain: | Negative. | |
| Physiology: | Positive with respect to catalase, oxidase, and the carbon and nitrogen sources listed below. | |
| Tolerance: | Can grow at temperatures up to and including 40° C. | |
| Growth Characteristics: | Will grow in oxygen-limited conditions. | |
| Carbon Sources on which ADP Bacterium grows: | Tween 40 | Tween 80 |
| | α-D-glucose | methyl pyruvate |
| | mono-methyl succinate | acetic acid |
| | aconitic acid | citric acid |
| | sodium citrate | formic acid |
| | D-gluconic acid | p-hydroxy phenylacetic acid |
| | α-hydroxybutyric acid | β-hydroxybutyric acid |
| | α-ketobutyric acid | α-ketoglutaric acid |
| | α-ketovaleric acid | D,L-lactic acid |
| | malonic acid | propionic acid |
| | quinic acid | succinic acid |
| | bromo-succinic acid | succinamic acid |
| | alaninamide | D-alanine |
| | L-alanine | L-alanylglycine |
| | L-asparagine | L-aspartic acid |
| | L-glutamic acid | glycyl-L-glutamic acid |
| | hydroxy-L-proline | L-ornithine |
| | L-proline | L-pyroglutamic acid |
| | L-serine | L-threonine |
| | D,L-carnitine | γ-aminobutyric acid |
| | urocanic acid | inosine |
| | phenyl ethylamine | putrescine |
| | 2-aminoethanol | |
| Carbon Sources on which ADP Bacterium will not grow: | cyclodextrin | dextrin |
| | glycogen | 1-erythritol |
| | D-fructose | 1-fucose |
| | D-galactose | gentiobiose |
| | α-D-lactose | m-inositol |
| | lactulose | maltose |
| | D-melibiose | β-methyl-D-glucoside |
| | D-psicose | D-raffinose |
| | L-rhamnose | D-sorbitol |
| | sucrose | D-trehalose |
| | turanose | xylitol |
| | D-γ-hydroxybutyric acid | glacturonic acid |
| | D-galactonic acid | D-glucosaminic acid |
| | galucuronamide | L-phenylalanine |
| | D-serine | uridine |
| | thymidine | 2,3-butanediol |
| Nitrogen Sources on which ADP Bacterium grows: | atrazine | desethylatrazine |
| | desisopropylatrazine | desethyldesisopropylatrazine |
| | hydroxyatrazine | desethylhydroxyatrazine |
| | cyanuric acid | ammonium nitrate |
| | potassium nitrate | potassium nitrite |
| | β-alanine | glutamic acid |

TABLE 1-continued

Characteristics of the ADP Bacterium

|                      | glutamine   | L-asparagine |
|                      | urea        | biuret       |
| Nucleotide Sequence: | See Table 2. |             |

Deposit of Representative
Microorganism Pseudomonas sp. ADP, American Type Culture Collection, Rockville Maryland, 20852 ATCC No. 55464, deposited August 13, 199.

The ADP bacteria of the present invention can be isolated from a mixed culture capable of degrading atrazine, and can be grown directly on media which contain the compounds to be decomposed. Alternatively, the ADP bacteria can be initially grown on a suitable growth medium and subsequently added to the samples containing the compounds to be decomposed. The optimum growth of the ADP bacterium takes place within a pH range of about 5.5–8.5, preferably about 7.0–7.5, and at a temperature of about 20°–40° C., preferably about 25°–37° C. Preferably, the ADP bacteria is isolated and then grown aerobically in a medium containing a source of carbon and a source of nitrogen.

A suitable growth medium contains at least about 0.4 mM inorganic or organic nitrogen-containing compounds, i.e., nitrogen source. In addition, the growth medium preferably contains at least about 15 mM of an oxidizable organic compound, i.e., carbon source, capable of being metabolized by the organism. The nitrogen source can be any of those nitrogen-containing compounds listed in Table 1. The carbon source can be any of those carbon-containing compounds on which the ADP bacteria will grow listed in Table 1. Preferably, the nitrogen source is an s-triazine compound and the carbon source is an organic acid which is an intermediate in the tricarboxylic acid cycle, such as, for example, sodium citrate or sodium succinate. More preferably, the nitrogen source is atrazine and the carbon source is sodium citrate. The growth of the bacteria on a selective medium containing atrazine as the sole nitrogen source and sodium citrate as the sole carbon source is particularly advantageous because this practically eliminates the risk of contamination by other microorganisms during growth. Thus, the biologically pure culture of a strain of the genus Pseudomonus of the present invention is characterized in that it exhibits sustained growth in media containing atrazine as the sole nitrogen source.

In addition, the bacterium can grow under oxygen limited conditions, i.e., in a culture which is not agitated such that oxygen does not readily diffuse into the culture. Thus, extensive aeration during the growth of the bacterium, as by agitation, is not necessary, and the contamination risk is further reduced. A representative example of the growth medium, referred to herein as the "atrazine medium," contains $K_2HPO_4$, $KH_2PO_4$, $MgSO_4 \cdot 7H_2O$, NaCl, $CaCl_2$, sucrose, sodium citrate, atrazine, various salts, and various vitamins. Example 3 provides a specific formulation for the atrazine medium.

The bacteria of the present invention permit highly effective detoxification of many types of s-triazine compound contamination, particularly samples of water, waste-water, and soil that are contaminated with atrazine. They provide a safe and effective means of detoxifying materials substantially completely, such that the detoxified materials contain no substantial amounts of toxic intermediates. That is, the bacteria of the present invention rapidly degrades s-triazine compounds to nontoxic materials, such as chloride ions, carbon dioxide, and ammonium ions. Thus, the biologically pure culture of a strain of the genus Pseudomonus of the present invention is characterized in that it can detoxify atrazine by degrading the triazine ring.

The present invention provides for substantially complete degradation of s-triazine compounds, preferably chlorinated s-triazine compounds, and more preferably atrazine. The initial concentrations of the s-triazine compound can range from trace amounts to thousands of pans per million (ppm). These values represent the initial concentration of the s-triazine in an aqueous solution containing the s-triazine compound, the bacterium, and the aqueous media. It is to be understood that a "trace" amount refers to the lower limit of detection of the assay techniques described in the examples below, which typically is approximately 2–3 parts per billion. As used herein "rapidly" and "substantially completely" means that about 90% of the initial concentration of the s-triazine compound in an aqueous solution is degraded in about 180 minutes. Preferably, the bacteria of the present invention can degrade about 95% of the initial concentration of the s-triazine compound in an aqueous solution in about 1200 minutes. Although the ADP bacterium of the present invention can degrade s-triazine compounds rapidly, e.g., on the order of hours and even minutes, in aqueous media, it is to be understood that the bacterium degrades such compounds in soil samples much more slowly, typically on the order of days and even weeks.

It is expected that a variety of methods known in the an could be employed to produce mutations of the biologically pure strain described herein that would also possess useful properties with respect to the degradation of atrazine or other s-triazine compounds. Thus, the present invention includes within its scope mutations of the ADP bacterium described herein that exhibit characteristics substantially the same as the ADP bacterium of the present invention.

Methods of Degradation of s-Triazine Compounds

The present invention provides for degradation of s-triazine compounds, preferably chlorinated s-triazine compounds, and more preferably atrazine, present in environmental samples in a wide range of concentrations. For example, the contaminants can be present in a sample in very high concentrations (e.g., 2000 ppm), such as those typically occurring in a spill site or in manufacturing wastewater, as well as in relatively low concentrations (200 ppb or lower) such as those occurring after minor spills or in run-off water. Moreover, the present invention provides for the degradation of atrazine and other such compounds using growing cells of the ADP bacterium of the present invention, as well as a nongrowing cell suspension, or enzymes produced from the isolated bacterium in the form of a cell-free extract. The ADP bacterium used in the methods of the present invention can be part of a biologically pure culture, or part of a mixed culture containing an assemblage of organisms.

A method of the present invention for degrading an s-triazine compound involves contacting a sample, such as a waste-water sample or a soil sample, containing therein a dissolved s-triazine compound, with an effective amount of an atrazine-degrading bacterium characterized as stated above (i.e., the ADP bacterium). Preferably, this method involves contacting the sample with an amount of ADP bacterium effective to substantially completely degrade the s-triazine compound at a rate of about 10 mmoles per hour per gram of cell protein. By "substantially completely" it is meant that all the s-triazine compound is decomposed according to the limits of analysis of conventional techniques.

In preferred embodiments of the method of the present invention, the atrazine degrading bacterium (ADP) is cultured under batch culture conditions in an atrazine medium so as to induce the atrazine degrading enzymes. The cultured ADP bacterium is then contacted with the environmental sample containing the s-triazine compound(s) to be degraded. As used herein, the phrase "batch culture" means that the ADP bacteria has been cultured in a suitable container or Erlenmeyer flask containing the atrazine medium described above. The mass of cell protein of the ADP is determined by the method described in Mandelbaum et al., *Appl. Environ. Microbiol.*, 59, 1695–1701 (1993), which is incorporated herein by reference. Briefly, this method involves reacting cell proteins with bicinchonic acid to produce a colored product which can be quantitatively determined spectrophotometrically. A known protein, bovine serum albumin, is used to generate a standard curve for quantitation purposes.

The s-triazine compound to be degraded by the present method is preferably contacted with an aqueous solution, i.e., aqueous medium, containing about 0.1–20 g/L of the ADP bacterium. The preferred aqueous media used in the present invention is referred to herein as atrazine medium, which is describe above. Other aqueous media, suitable for use in the present invention may include, for example, media containing atrazine as a sole nitrogen source and sodium citrate as the main carbon source. We have found that the degradation of atrazine is stimulated by the presence of atrazine as the sole nitrogen source and is inhibited by the presence of additional nitrogen sources, such as ammonium nitrate or ammonium phosphate. It seems that the degradative enzymes are not constitutively expressed but are rather induced by atrazine and repressed by the presence of other nitrogen sources.

Nongrowing cells of the bacterium can also degrade atrazine at rates exceeding 10 mmoles per hour per gram of cell protein. To prepare the nongrowing cells, the bacterium is preferably cultured in flasks containing about 300 mL of a buffered salt medium containing sodium citrate as the carbon source and atrazine as the nitrogen source. After the bacteria have grown in the medium, they are washed and resuspended in 0.1N phosphate buffer (pH=7.0). Thes nongrowing cells can then be used to degrade atrazine and other s-triazine compounds. It is believed that during the culture, the bacteria produce enzymes that can hydrolyze the carbon-chlorine bond in the 2 position and further degrade the resulting transient metabolite hydroxyatrazine. Eventually, the s-triazine ring is cleaved and the ring carbons are liberated as $CO_2$.

Cell-free crude extract preparation from the ADP also effectively degrades atrazine. Accordingly, the present invention envisions a method of degrading s-triazine compounds by growing the bacterium in a batch culture and exposing the bacterium to conditions that stimulate the yield of atrazine degrading enzymes as discussed above. The bacterium thus cultured comprises enzymes to substantially completely degrade atrazine. Separating the bacterium from the medium using a centrifuge, breaking the cells to yield a crude extract and separating the cell debris using a centrifuge followed by filtering through 0.2 μm filter yield the cell-free crude extract preparation. An effective amount of this cell-free crude extract can be added to an aqueous slurry of atrazine to form a mixture and reacting the mixture for a period of time sufficient to substantially completely degrade the atrazine.

Solid material, such as soil, landfill material, and wood chips or shavings, can be decontaminated either by the direct addition of the bacterium to an aqueous slurry of the solid material, or by an extractive process that is preferably operated so as to bring the bacteria of the present invention into contact with aqueous solutions containing s-triazine compounds. Preferably the solid material is slurried or leached with water to remove the s-triazine compounds therefrom and form a leachate. To increase the amount of solid material that can be detoxified with a given volume of leachate, the leachate is preferably continuously or intermittently recycled through the solid material with pH-controlled water containing the ADP bacterium.

The invention will be further described by reference to the following detailed examples. These examples are offered to further illustrate the various specific and preferred embodiments and techniques. It should be understood, however, that many variations and modifications may be made while remaining within the scope of the present invention.

EXPERIMENTAL EXAMPLES

Example 1

Culturing and Isolation of ADP Bacterium

Soil samples were collected from a Little Falls, Minn. site which was formerly operated as an agricultural chemical dealership and was being considered for bioremediation. The native soil was a loamy sand containing about 90% sand with the remainder being silt and clay. Twelve cores (1.9 cm [inner diameter] by 30 cm deep) were collected at random locations at the site and stored at 4° C. until they were used. Some grassy weeds were also collected from the boundaries of the site for isolation of potential atrazine-degrading microorganisms from the rhizoplane.

Selective enrichment cultures were used to obtain mixed bacterial populations that were capable of growth on atrazine as a nitrogen source. Atrazine, metolachlor, and alachlor concentrations in soil samples were analyzed as described by W. C. Koskinen et al., (*Soil Sci. Soc. Am. J.*, 55, 561–562 (1991)), which is incorporated herein by reference. For samples that contained one or more herbicides, 10 g of soil was suspended three times in 30 mL of 0.1M phosphate buffer (pH 7.3) and centrifuged at 7,000×g for 10 minutes at 4° C., and the supernatants were discarded to reduce the quantity of extraneous nitrogen source(s).

To obtain enrichment cultures of weed rhizoplane microorganisms, loose soil particles were removed by hand, and the roots were submerged for 10 minutes in tap water, rinsed for 1 minute under slowly running tap water, and air dried. Roots were cut into 5 cm segments, and 10 segments were shaken in a 250 ml Erlenmeyer flask with 10 g of glass beads (diameter, 3 mm) and 50 mL of 0.1M phosphate buffer on a reciprocal shaker for 2 hours. Enrichment cultures were prepared as described below by using 5 mL of the buffer as inoculum.

A 5 g wet soil pellet or 5 mL of a rhizoplane suspension was inoculated into 20 ml of atrazine medium prepared as described in Example 3 below, except that 2.5 mL of an atrazine stock solution (20 mg/mL) was used. Cycloheximide (50 mg/L) was added to media used for isolation of bacteria, and the pH was adjusted to 7.3. The media used for isolation were acidified to pH 5.5 with a concentrated HCl solution, but were not amended with antibiotics. Cultures were incubated without shaking at 30° C. in the dark to preclude photolysis reactions. All enrichment cultures were subcultured into a homologous medium at 2-week intervals. From a 2-week-old culture, 0.5 mL was transferred to 20 mL of freshly prepared atrazine medium. After cultures were subcultured four times under conditions of nitrogen limitation, atrazine degradation was quantified by high-performance liquid chromatography (HPLC). Positive enrichment cultures were harvested by centrifugation, resuspended in buffer, and either frozen at −20° C. or amended with 20% glycerol (by volume) and stored at −70° C.

A mixed culture containing an assemblage of microorganisms, including the isolated Pseudomonas strain of the present invention, consumed 100% of a 100 ppm atrazine sample within about 5–7 days, as determined by HPLC, during a sixth subculture. Furthermore, extensive conversion, about 70–85%, of the $^{14}$C-labeled s-triazine ring carbon atoms to $^{14}CO_2$ was observed.

The ADP bacterium of the present invention was isolated from a mixed culture capable of degrading atrazine after subculturing 12+ times. Specifically, an atrazine-degrading mixed culture was transferred more than 12 times into growth medium containing atrazine as the sole source of nitrogen. Bacteria from a liquid culture were spread onto an agar plate containing 1000 ppm atrazine that formed a cloudy suspension of the herbicide. Bacterial colonies degrading atrazine were detected by observing a clear zone.

Example 2

Identification of ADP Bacterium

The species of the ADP bacterium of the present invention was identified using several methods. These included a bacteria identification system available from Biolog, Inc. (3938 Trust Way, Hayward, Calif. 94545), a fatty acid profile analysis, and a 16S rRNA (small sub-unit) profile.

Method A: Biolog, Inc. Bacteria Identification System

The Biolog, Inc. bacteria identification system for identifying the bacterium of the present invention is a gram negative microplate assay. The assay uses a 96-well microplate designed to test the ability of the inoculated microorganism to utilize (oxidize) a panel of 95 different carbon sources. When oxidation occurs, reduction of a tetrazolium dye produces a purple color (positive growth). These results are compared to a data-base of nearly 800 bacteria.

The bacterium was grown on TSA medium according to the instructions in the Biolog, Inc. manual. The plates were incubated at 30° C. in the dark and readings were made 24 hours after inoculation. The unknown ADP bacterium was identified as *Pseudomonas citronellolis* with a similarity index of 0.554, distance of 6.767, average of 0.234, and maximum at 2.931. Other possible species were *Pseudomonas nitroreducens* and *Pseudomonas aeruginosa* but the similarity index was only 0.007 and 0.001, respectively. A similarity value of 0.5 and above is considered by the manufacturer of the kit as a positive identification.

Method B: Fatty Acid Profile Analysis

A culture of *Pseudomonas citronellolis* was purchased from the American Type Culture Collection (ATCC #13674) and was subjected to a fatty acid analysis, as was a culture of ADP. Briefly this method involved the extraction of the total phospholipids using chloroform and methanol (2:1). Methyl esters of the phospholipid fatty acids were prepared and analyzed by capillary gas-liquid chromatography. Fatty acid profiles were prepared by compiling the chain lengths, degrees of unsaturation, and positions of double bonds. Using this method the unknown ADP bacterium was identified as a *Pseudomonas aeruginosa* with a similarity index of 0.530. The *Pseudomonas citronellolis* was also identified as a *Pseudomonas aeruginosa* but with a lower similarity index of 0.323. A similarity index of 0.400 or higher indicates a very good match to the microbial identification system database; 0.250 or lower indicates a poor profile match. Profiles that are different in more than 0.1 similarity index units are considered to be different, indicating that the ADP is closely related to *Pseudomonas aeruginosa* but probably is not a *Pseudomonas citronellolis*.

Method C: 16S rRNA (small sub-unit) Profile

Ribosomal RNA (rRNA) appears to be the choice for molecular biological approaches to phylogeny. rRNA sequences are in most cases species specific and independent of growth and physiological changes. Thus, they are useful tools for identification of bacteria. See, for example, Woese, *Microbiological Reviews*, 51, 221–271 (1987). In order to further identify the atrazine degrading microorganism, the 16S rRNA of ADP and that of the *Pseudomonas citronellolis* (ATCC #13674) were analyzed. Sequence analysis data have also been compared with existing data from GenBank on the 16S rRNA sequence of *Pseudomonas aeruginosa* and two other Pseudomonas sp. The sequences were also compared to that of *Escherichia coli*.

Cell lysis and total RNA isolation from ADP and *Pseudomonas citronellolis* were accomplished as described below. Into 2.2 mL screw-cap conical vials on ice were loaded: 0.7 mL backed Zirconium beads (75–200 gm), 0.8 mL bacterial sample in buffer (about 100 mg cell wet weight/mL), 50μL 20% SDS and 0.7 ml phenol at pH 5.1. The vial was shaken for two minutes in a bead beater (maximal speed) and then incubated 10 minutes at 60° C. The aqueous phase and phenol were separated by centrifugation. The aqueous phase containing the RNA was immediately frozen. Seven synthetic 16S rRNA-specific oligonucleotide primers, which mimic conserved sequence regions of the 16S rRNA molecules of *E. coli* were used as previously described by Tsuji et al., *J. General Microbial.*, 136, 1–10 (1989). Sequence alignment data are given in Table 2. Homology data analysis is presented in Table 3.

TABLE 2

Sequence Alignment of 16S Ribosomal RNA For:

1 (Ecoli): *Escherichia coli*
2 (ADP): Atrazine-Degrading Isolate
3 (PCA): *Pseudomonas citronellolis*
4 (aerugino): *Pseudomonas aeruginosa*
5 (testost): *Pseudomonas testosteroni*
6 (cepacia): *Pseudomonas cepacia*

| Position | Sequence identity | | Data |
|---|---|---|---|
| 1 | 1 Ecoli | (SEQ ID NO:1) | AAAUUGAAG AGUUGAUCA UGGCUCAGAU UGAACGCUGG CGGCAG– GCC UAACACAUGC AAGUCGAACG GU– AACAC– G GAAGAAGCUU Ecoli |
| 1 | 2 ADP | (SEQ ID NO:2) | NUGAAG AGUUGAUCA UGGCUCAGAU UGAAUUGUGG CGGUUAGGCC UAACACAUGC AAGUCGAGCG GAUGA–A–– G GGAGCUUGCU ADP |
| 1 | 3 PCA | | PCA |
| 1 | 4 aerugino | (SEQ ID NO:6) | AUACUGAAG AGUUGAUCA UGGCUCAGAU UGAACGCUGG CGGCAG– GCC UAACACAUGC AAGUCGAGCG GAUGA–A–– G GGAGCUUGCU aerugino |
| 1 | 5 testost | (SEQ ID NO:7) | GAACUAUAG AGUUGAUCC UGGCUCAGAU UGAACGCUGG CGGCAU– GCU UUACACAUGC AAGUCGAACG GU– AACA– G G–– UCUUC–– testost |
| 1 | 6 cepacia | (SEQ ID NO:8) | NNACUGAAG AGUUNAUCC UGGCUCAGAU UNAACGCUGG CGGCAU– GCC UUACACAUGC AAGUCGAACG GC– AGCAUCG GUGCUUNCA cepacia |
| 114 | 1 Ecoli | | GCUUC–– UUU GCUGACGAGU GGCGGACGGG UGAGUAAUGU CUGGGAAACU GCCUGAU– GG AGGGGGAUAA CUACUGGAAA CGGUAGCUAA Ecoli |
| 114 | 2 ADP | | UCCCGGAUUU –AG–– CG– GC GG––– AUGGG UAGUAAUGU CUAGGAAUCU UGGGGACAA CGUUGGAAUCU GCGUUGGAAUC CUAGGAAUCU GGAGCGCUAA ADP |
| 114 | 3 PCA | | (SEQ ID NO:3) GGAHUCU GCCUBGU– AG UGGGGGACAA CGUUCCGAAA YGAGCGCUAA PCA |
| 114 | 4 aerugino | | –CCUGGAUU– CAG–– CG– GC GG––– ACGGG UGAGUAAUGC CUAGGAAUCUG UGGGGAAUAA CGUUCCGAAA CGGGCGCUAA aerugino |
| 114 | 5 testost | | ––– GGAU– G CUGA– CGAGU GGCGAACGGG UGAGUAAUGU CUAGGAAUAUC AUCGGAAUCGU GCCGAAAA CUACUCGAAA GAGUAGCUAA testost |
| 114 | 6 cepacia | | CC–––– UN– GUGG– CGAGU GGCGAACGGG UGAGUAAUAC AUCGGAACAU GUCCUGU– AG UGGGGGAUAA C– CGGCGAAA GCCNNAUUAA cepacia |
| 209 | 1 Ecoli | | UACCGCAUAA CGUCGC–AGA CCAAAGAGGG GGACCUUCGG GCCUCUUGCC AUCGGAUGUG CCCAGAUGGG AUUAGCUAGU AGGUGGGGUA Ecoli |
| 209 | 2 ADP | | UACCGCAUAC GUCCUCCGGG AGAAAGUGGG GGAUCUUCGG ACCUCACGCU AUCCSAUGCU AUGANAUGAG CCUAGGCUGU AUUAGCUAGU AGGUGGGGUA ADP |
| 209 | 3 PCA | | UACCGCAUAC GUCCUACGGG AGAAAGGGGG GGAUCUUCGG ACCUCUCGG ACCUCACGCU AUCNGAUGCU AUGANAUGAG CCUAGGUCUG AUUAGCUAGU UGGUGGGGUA PCA |
| 209 | 4 aerugino | | UACCGCAUAC GUCCUACGGG AGAAAGGGGG GGAUCUUCGG ACCUCCUCGG GCCUUGUGCU AUAGGAGGCG CUGAUGGCAG AUUAGCUAGU UGGUGGGGUA aerugino |
| 209 | 5 testost | | UACCGCAUAC GAUCUACGGG AGAAAGGGGG GAUCUACGGG GCCUUUGUCU ACUAGGAGCG CUGAUGUGCU AUAGGCUGUA AUUAGCUAGU UGGUGGGGUA testost |
| 209 | 6 cepacia | | UACCGCAUAC GAUCUACGGG NGAAAGCGGG GGAUCUUCGG GCCUUGUGCU AUAGGAGCG AUGAAGUGG CCGAUGGCUG AUUAGCUAGU UGGUGGGGUA cepacia |
| 312 | 1 Ecoli | | ACGGCUCACC UAGGCGACGA UCCCUAGCUG GUCUGAGAGG AUGACCAGCC ACACUGGAAC UGAGACACGG UCCAGACUCC UACGGGAGGC Ecoli |
| 312 | 2 ADP | | AUGGCUCACC UAGGCGACGA UCCGUAACUG GUCUGAGAGG AUGACCAGCC ACACUGGAAC ACACUGGAAC UGAGACACGG UCCAGUCUCC UACGGGAGGC ADP |
| 312 | 3 PCA | | AUGGCUCACC UAGGCGACGA UCCGNAACUR GUCUGAGAGG AUGAUCAGCC ACACUGGAAC UGAGACACGG UCCAGYUCCC UACGGHGGC PCA |
| 312 | 4 aerugino | | AAGGCUACC AAGGCGACGA UCCGUAACUG GUCUGAGAGG ACGACCAGCC ACACUGGAAC UGAGACACGG UCCAGACUCC UACGGGAGGC aerugino |
| 312 | 5 testost | | AAGGCUUACC AAGCCUGGA UCUGUAGCUG UCAGUAGCUN AUGGGCGCA AGCCUGGAC AGCACCAGCC ACACUGGGAC UGAGACACGG CCCAGACUCC UACGGGAGGC testost |
| 312 | 6 cepacia | | AAGGCUCACC AAGGCCUGGA AAUAUUGGAC CAUGGGCGAA AGCCUGGAC AGCCUGGAC ACGACCAGCC ACACUGGACC CGUGAUGAA GAAGGCCUUC GGUUGUAAA GUACUCCAG cepacia |
| 403 | 1 Ecoli | | AGCAGUGGGG AAUAUUGGAC AUGGGCGAA AGCCUGAUCC AGCCAUGCCG CGUGUAUGAA GAAGGCCUUC GGGUUGUAAA GUACUUUCAG Ecoli |
| 403 | 2 ADP | | AGCAGUGGGG HAUAUUGGAC AUGGGCGAA AGCCNGAUCC AGCCAUGCCG CGUGUGUGAA GAAGGUCUUC GGAUUGUAAA GCACUUUAAG ADP |
| 403 | 3 PCA | | AGCAGUGGGG AAUAUUGGAC AUGGGCGAA AGCCUGAUCC AGCCAUGCCG CGUGUGUGAA GAAGGCCCUC GGAUUGUAAA CUGCUUUGU PCA |
| 403 | 4 aerugino | | AGCAGUGGGG AAUUUGGAC AUGGGCGAA AGCCUGAUCC AGCCAUGCCG CGUGCAGGAU GAAGGUCUUC GGAUUGUAAA CUGCUUUGU aerugino |
| 403 | 5 testost | | AGCAGUGGGG AAUUUUGGAC AUGGGCGAA AGCCAUGCCG CGUGUGUGAU AUGAAGGCCUUC GGAUUGUAAA GCACUUUAAG testost |
| 403 | 6 cepacia | | AGCAGUGGGG AAUUUGGAC AUGGGCGAA AGCCUGAUCC AGCCAAUGCCG CGUGAAUGAA GAAGGCCUUC GGGUUGUAAA GCACUUUUGU cepacia |
| 494 | 1 Ecoli | | CGGGGAGGAA GGGAGUAAAG UUAAUACCUU UGCUCAUUGA CGUUACCCGC AGAAGAAGCA CCGGCUAACU CCGUGCCAGC AGCCGCGGUA Ecoli |
| 494 | 2 ADP | | UUGGGAGGAA GGGCAGUAAG UUAAUACCUU GCUNUUUGA GCUNUUUGA GCUAAUACCUU GCUAACCAAC AGAAUAAGCA CCGGCUAACU UCGUGCCAGC AGCCGCGGUA ADP |
| 494 | 3 PCA | | UUGGGAGGAA GGGCAGUAAG UUAAUACCUU UUAAUACCUU GCUUAACUU GCUAACCAAC AGAAUAAGCA CCGGCUAACU CCGUAACU (SEQ ID NO:4) GUA PCA |
| 494 | 4 aerugino | | UUGGGAGGAA GGGCAGUAAG UUAAUACCUU GCUGUUUUGA CGUUACCAAC AGAAUAAGCA CCGGCUAACU UCGUGCCAGC AGCCGCGGUA aerugino |
| 494 | 5 testost | | ACGAACGAA AAGCCUGGGG AUCCCUGGGCU CUAAUAUCCC CGGGUCACAGC GUACGGA AGAAUAAGCA CCGGCUAACU ACGUGCCAGC AGCCGCGGUA testost |
| 494 | 6 cepacia | | CCGGGAAGAA AUCCUUGGUC CGGGUCACGA AGAAUAAGCA CCGGCUAACU ACGUGCCAGC AGCCGCGGUA cepacia |
| 586 | 1 Ecoli | | AUAC– GGAGG GUGC– AAGCG UUAAU– CGGA AUUACUGGGC GUAAGAGCGC ACGCAGGCGG UUUGUAAGUC AGAUGUGAAA UCCCCGGGCU Ecoli |
| 586 | 2 ADP | | AUAC– GAAGG GUGC– UAGCG UUAAU– CGGA AUUACUGGGC GUAAAGCGCG CGUAGGUGGU UUGUUAAGAU GGAUGUGAAA UCCCCGGGCU ADP |
| 586 | 3 PCA | | AUAC– GAAUG GUGCAAGCG UUAAUUCGGA AUUACUGGGC GUAAGCGCG CGUAGG–UKU UUGGUAAGAU GGAUGUGAAA UAAAGGGCU PCA |
| 586 | 4 aerugino | | AUAC– GAAGG GUGC– GAGCG UUAAU– CGGA AUUACUGGGC GUAAGCGCG CGUAGGUGGU UCAGCAAGUU GGAUGUGAAA UCCCCGGGCU aerugino |

TABLE 2-continued

Sequence Alignment of 16S Ribosomal RNA For:

1 (Ecoli): *Escherichia coli*
2 (ADP): Atrazine-Degrading Isolate
3 (PCA): *Pseudomonas citronellolis*
4 (aerugino): *Pseudomonas aeruginosa*
5 (testost): *Pseudomonas testosteroni*
6 (cepacia): *Pseudomonas cepacia*

| Position | Sequence identity | Data |
|---|---|---|
| 586 | 5 testost | AUAC- GUAGG GUGC- AAGCG UUAAU- CGGA AUUACUGGGC GUAAAGCGUG CGCAGGCGGU UUUGUAAGAC AGUGGUGAAA UCCCCGGGCU |
| 586 | 6 cepacia | AUAC- GUAGG GUGC- AAGCG UUAAU- CGGA AUUACUGGGC GUAAAGCGUG CCCAGGCGGU UCAUGUGAAA UCCCCGGGCU |
| 676 | 1 Ecoli | CAACCUGGGA ACUGCAUCUG ACUGCAUCCA UACACUCCUG ACUAGAGGUCU -CGUAGAGGG GGGUAGAAUU CCAGGUGUAG CGGUGAAAUG CGUAGAUAUA |
| 676 | 2 ADP | CAACCUGGGG ACUGCAUCUG ACUGCAUCCA UACACUCCUG ACUAGAGGAC -GGUAGAGGG UGGUGGAAUU UCCGGUGUAG CGGUGAAAUG CGUAGAUAUA |
| 676 | 3 PCA | CAACCUGGUW ACUGCAGGUW ACUGCAUCCN UAACACUCUGA ACUAGAGGUAC GUGUAGUAGGG UGGUGAAUU UC |
| 676 | 4 aerugino | CAACCUGGGA ACUGCAUCCN AAACUACUGA ACUAGCAUUG GACUCGCAAG GCUAGAGUC- GGCAGAGGG GGAUGGAAUU CCGGGGUGUAG CGGUGAAAUG CGUAGAUAUA |
| 676 | 5 testost | CAACCUGGGA ACUGCAUUG ACUGCAUUGG UGACUGGCAAG UGACUGGCAG GCUAGAGUAU- GGCAGAGGG GGGUAGAAUU CCACGUGUAG CAGUGAAAUG CGUAGAUAUG |
| 676 | 6 cepacia | CAACCUGGGN ACUGCAUGGG UGACUGGCAAG UGACUGGCAG GCUAGAGUAU- GNNAGAGGG GGGUAGAAUU CCACGUGUAG CAGUGAAAUG CGUAGAUAUG |
| 766 | 1 Ecoli | UGGAGGAAUA CCGGUGGCGA AGGCGGCCCC CUGGACGAAG ACUGACGCUC AGGUGCGAAA GCGUGGGGAG CAAACAGGAU UAGAUACCCU |
| 766 | 2 ADP | GGAAGGAACA CCAGUGGCGA AGGCGGACCA CCUGGACUGA ACUGACGCUG AGGUGCGAAA GC- UGGGGAG CMAACAGGAU UAGAUACCCU |
| 766 | 3 PCA | (SEQ ID NO:5) A AGGCGACCAC CU- GACUGAU ACUGACACUG AGGUGCGAAA GCGUGGGGAG CAAACAGGAU UAGAUACCCU |
| 766 | 4 aerugino | GGAAGGAACA CCAGUGGCGA AGGCGGACCAC CUGGACCUGA ACUGACACUG AGGUGCGAAA GCGUGGGGAG CAAACAGGAU UAGAUACCCU |
| 766 | 5 testost | CGGAGGAACA CCGAUGGCGA AGGCAGCCCC CUGGGCCAAU ACUGACGCUC AUGCACGAAA GCGUGGGGAG CAAACAGGAU UAGAUACCCU |
| 766 | 6 cepacia | UGGAGGAAUA CCGAUGGCGA AGGCAGCCCC CUGGGCCCAAU ACUGACGCUC AUGCACGAAA GCGUGGGGAG CAAACAGGAU UAGAUACCCU |
| 856 | 1 Ecoli | GGUAGUCCAC GCCGUAAACG AUGUCGACUU GGAGGUUGU CCC- UUGA- G GCGUGGCUUC CGGAGCUAAC GCGUUAAGUC GACCGCCUGG |
| 856 | 2 ADP | GGUAGUCCAC GCCGUAAACG AUGUCGACUA GCCG- UUGGG AUCCUUGGGA UCUUAGU- GG CGCA- GUAAG GCGAUAAGUC GACCGCCUGG |
| 856 | 3 PCA | GGUAGUCCAC GCCGUAAACG AUGUCGACUA GCCG- UUGGG AUC- UUGGGA UCUUAGU- GG CGCACGUAAC GCGAAAAGUC GACCGCCUGG |
| 856 | 4 aerugino | GGUAGUCCAC GCCGUAAACG AUGUCGACUA GCCG- UUGGG- UUGGG -UC- UUAACU CUCUAGUA- GG CGAAGUAAC GCGUAAGUU GACCGCCUGG |
| 856 | 5 testost | GGUAGUCCAC GCCUUAAACG AUGUCAACUG GUUG- UUGGG -UC- UUAACU CUCAAGU- GG CGCAGCUAAC GCGUGAAGUU GACCGCCUGG |
| 856 | 6 cepacia | GGUAGUCCAC GCCUAAACG AUGUCAACUA GUUG- UUGGG GA-- UUCAUU UCCUUAGUAA CGUAGCUAAC GCGUGAAGUU GACCGCCUGG |
| 948 | 1 Ecoli | GGAGUACGGC CGCAAGGUUA AAACUCAAAU GAAUUGACGG GGGCCCGCAC AAGCGGUGGA GCAUGUGGUU UAAUUCGAUG CAACGCGAAG |
| 948 | 2 ADP | GGCGUACGGC CGCAAGGUUA AAACUCAAAU GA- UUCA- GG GGG- CCGCAC AACCGGUGGA GCAUGUGGUU UAAUUCGAAn NAACGCGAAG |
| 948 | 3 PCA | GGAGUACGGC CGCAAGGUUA AAACUCAAAU GACUUUACGG GGG- CCGCAC AACCGGUGGA GCAUGUGGUU UAAUUCGAAn NAACGCGAAG |
| 948 | 4 aerugino | GGAGUACGGC CGCAAGGUUG AAACUCAAAU GAAUUGACGG GGGCNNGCAC AAGCGGUGGA GCAUGUGGUU UAAUUCGAAG CAACGCGAAG |
| 948 | 5 testost | GGAGUACGGC CGCAAGGUUG AAACUCAAAG GAAUUGACGG GGACCCGCAC AAGCGGUGGA UGAUGUGGUU UAAUUCGAUG CAACGCGAAA |
| 948 | 6 cepacia | GGAGUACGGU CGCAAGGAUUA AAACUCAAAG GAAUUGACGG GGACCCGCAC AAGCGGUGGA UGAUGUGGAU UAAUUCGGAU NAACGCGAAA |
| 1044 | 1 Ecoli | AACCUUACCU GGCCUUGACA U- CCACGGAA GUUUUCAGAG AUGAGAAUGU UGC- CUUCGG -GAACCUGA GACAGGUGCU GCAUGGCUGU |
| 1044 | 2 ADP | AACCUUACCU GGCCUUGACA UG- UCGGAA UCGGAGAGAG CAUGCGAGAG Y- C- CUUCGG -GAAUCGGAA CACAGGUGCU GCAUGGCUGU |
| 1044 | 3 PCA | AACCUUACCU GGCCUUGACA UG- UCGGAA UUCUGUAGAG AUACAGAG UGC- CUUCGG -GAACCGA GACAGGUGCU GCAUGGCUGU |
| 1044 | 4 aerugino | AACCUUACCU GGCCUUGACA UG- UCGGAA UCCUGCAGAG AUGCGGAG UGCCCUUCGG -GAACCGA GACAGGUGCU GCAUGGCUGU |
| 1044 | 5 testost | AACCUUACCC ACCUUGACA UG- GCAGAA CUUUCCAGAG -AUGGAUUGG UGCCUUCGG -GAACCUGA GACACAGGUGCU GCAUGGCUGU |
| 1044 | 6 cepacia | AACCUUACCU ACCUUGACA UG- GUCGGAA UCCUGCUGAG -AGGCGGGAG UGCUCGAAAG AGAACCGGCG CACAGGUGCU GCAUGGCUGU |
| 1136 | 1 Ecoli | CGUCAGC- UC -GUG- UUGUG AAAUGUUUGG UUAAGUCCCG CAACGAGCGC AACCCUUAUC CUUUGUUGCC AGC- GGUCCG GCCGGGAACU |
| 1136 | 2 ADP | CGUCAGGHUC AGUGGCGUG AGAUGUUGGG UUAAGUCCGC UAACGAGCGC AACCCUUGUC CUUAGUUACC AGCAGGUCACU |
| 1136 | 3 PCA | CGUCAGC- UC AGUGGCGUGA UUAUGUUGGG UUAAGUCCGC AACGAGCGC AACCCUUGUC CUUAGUUGCC AGCACGUUAU GGUGGCGUGU |
| 1136 | 4 aerugino | CGUCAGC- UC -GUG- UCGUG AGAUGUUGGG UUAAGUCCGC AACGAGCGC AACCCUUGUC CUUAGUUACC AGCAC- CUCG GGUGGCACU |
| 1136 | 5 testost | CGUCAGC- UC -GUG- UCGUG AGAUGUUGGG UUAAGUCCGC AACCCUUGCC AUUAGUUGCU A- CA-- UUCA GUGAGCACU |
| 1136 | 6 cepacia | CGUCAGC- UC -GUG- UCGUG AGAUGUUGGG UUAAGUCCGC AACCCUUGUC CUUAGUUGCU A- CGC- -- NA --- GAGCACU |
| 1232 | 1 Ecoli | CAAAGGAGAC UGCCAGUGA- UAAACUGGA- GGAAGGUGGG GAUGACGUCA AGUCAUCAUG GCCCUUACGA GCCCUUACGA GCCCUACGA ACACGUGCUA |
| 1232 | 2 ADP | CUUAAGAGAC UGCCGGUGAC -AAACCGGAG GAAGGUGGG GAUGACGUCA AGUCAUCAUG GCCCUUACGG CCAGGGCUAC ACACGUGCUA |
| 1232 | 3 PCA | CUAAGGAGAC UGCCGGUGAC UAAACCGGA- GGCAGGYGGG GAUGACGUCA AGUCAUCAU- --- CCUUACGG CYAGGGCUAC ACACGUGCUA |

TABLE 2-continued

Sequence Alignment of 16S Ribosomal RNA For:

1 (Ecoli): *Escherichia coli*
2 (ADP): Atrazine-Degrading Isolate
3 (PCA): *Pseudomonas citronellolis*
4 (aerugino): *Pseudomonas aeruginosa*
5 (testost): *Pseudomonas testosteroni*
6 (cepacia): *Pseudomonas cepacia*

| Position | Sequence identity | Data |
|---|---|---|
| | | CUAAGGAGAC UGCCGGUGAC –AAACCGGA– GGAAGGUGGG GAUGACGUCA AGUCAUCAUG GCCCUUACGG CNAGGGCUAC ACACGUGCUA aerugino |
| 1232 | 4 aerugino | CUAAGGAGAC UGCCGGUGAC –AAACCGGA– GGAAGGUGGG GAUGACGUCA AGUCCUCAUG GCCCUAUAG GUGGGCUAC ACACGUCAUA testost |
| 1232 | 5 testost | CUAAGGAGAC UGCCGGUGAC –AAACCGGA– GGAAGGUNGG GAUGACGUCA AGUCCUCAUG GCCCUAUGG GUAGGGCUUC ACACGUCAUA cepacia |
| 1232 | 6 cepacia | CAAUGGCGCA UACAAA– GAG AAGCG– ACCU CGCGAGAGCA AGCGGACCU– CAUAAAGUGC GUCGUAGUCC GGAUUGGAGU CUGCAACUCG Ecoli |
| 1327 | 1 Ecoli | CAAUGGUCGG UACAGA– GGG UUGCC– AAGC CGCGAGGUGG AGCUAAUC– C CAGAAAACCG AUCGUAGUCC GGAUCGCAGU CUGCAACUCG ADP |
| 1327 | 2 ADP | CAAUGGUCGG UACAGACGGG UUGCCCAAGC CGAGAGGUCG ASCUAAUC– C CAGAAAACCG AUCGUAGUCC GGAUCGCAGU CUGCAACUCG PCA |
| 1327 | 3 PCA | CAAUGGUCGG UACAAA– GGG UUGCG– AAGC CGCGAGGUGG AGCUAAUC– C CAUAAAACCG AUCGUAGUCC GGAUCGCAGU CUGCAACUCG aerugino |
| 1327 | 4 aerugino | CAAUGGUCGG UACAAA– GGG UUGCC– AACC CGCGAGGGGG AGCUAAUC– C CAGAAAACCG AUCGUAGUCC GGAUCGCAGU CUGCAACUCG testost |
| 1327 | 5 testost | CAAUGGUCGG AACAGA– GGG UUGCC– AACC CGCGAGGUGG AGCUAAUC– C CAGAAAACCG AUCGUAGUCU GGAUUGCACU CUGCAACUCG cepacia |
| 1327 | 6 cepacia | ACUCCAUGAA GUCGGAAUCG CUAGUAAUCG UG– GA– UCAG AAUGCCACGG UGAAUACGUU CCCGGCCCUU GUACACACCG CCCGUCACAC Ecoli |
| 1418 | 1 Ecoli | ACUGCGUGAA GUCGGAAUCG CUAGUAAUCG UG– – AAUCAG AAUGUCACGG UGAAUACGUU CCCGGCCCUU GUACACACCG CCCGUCACAC ADP |
| 1418 | 2 ADP | ACUGCGUGAA GUCGGAAUCG CUAGUAAUCG UGUGAAUCAG AAUGUCACGG UGAAUACGUU CC PCA |
| 1418 | 3 PCA | ACUGCGUGAA GUCGGAAUCG CUAGUAAUCG UG– – AAUCAG AAUGUCACGG UGAAUACGUU CCCGGGCCUU GUACACACCG CCCGUCACAC aerugino |
| 1418 | 4 aerugino | ACUGCGUGAA GUCGGAAUCG CUAGUAAUCG UG– GA– UCAG AAUGUCACGG UGAAUACGUU CCCGGUCUU GUACACACCG CCCGUCACAC testost |
| 1418 | 5 testost | AGUGCAUGAA GUCGGAAUCG CUAGUAAUCG CG– GA– UCAG CAUGCGCGG UGAAUACGUU CCCGGGCUU GUACACACCG CCCGUCACAC cepacia |
| 1418 | 6 cepacia | CAUGGGAGUG GGUUGCAAAA GAAGUAGGUA GCUUAACCUU CGGGAGGGCG CUUACCACUU UGUGAUUCAU GACU– GGGGU GAAGUCGUAA Ecoli |
| 1508 | 1 Ecoli | CAUGGGAGUG GGUUGCUCCA GAAGUAGCUA GCUUAACCGC AAGGGGGACG GUUACCACGG GUACCACACG AGUGAUU ADP |
| 1508 | 2 ADP | CAUGGGAGUG GGUUGCUCCA GAAGUAGGUA GCUUAACCGC AAGGGGGACG GUUACCACGC AGUGAUUCAU GNNNNNNNNN NNNNNGUAAC PCA |
| 1508 | 3 PCA | CAUGGGAGCG GGUCUCCCA GAAGUAGGUA GCCUAACCGU AAGGAGGGCG CUUACCACGG CGGGUUCGU GACU– GGGGU GAAGUCGUAA aerugino |
| 1508 | 4 aerugino | CAUGGGAGUG GGUUUUACCA GAAGUGGCUA GCUUAACCAC AAGGAGGANN GUCACNANGG UAGGAUNAN G testost |
| 1508 | 5 testost | CAAGGUAACC GUAGGGGAAC CUGCGGUUGG AUCACCUCCU UA Ecoli |
| 1508 | 6 cepacia | | ADP |
| 1603 | 1 Ecoli | | PCA |
| 1603 | 2 ADP | AAGNNNNNNN NNNNNGAACC UG aerugino |
| 1603 | 3 PCA | CAAGGUAGCC GUAUCGGAAG GUGCGGCUGG AUCACCUCCU UUCU testost |
| 1603 | 4 aerugino | | cepacia |
| 1603 | 5 testost | | |
| 1603 | 6 cepacia | | |

TABLE 3

Homology Data Analysis 1 (Ecoli): *Escherichia coli*
2 (ADP): Atrazine-Degrading Isolate
3 (PCA): *Pseudomonas citronellolis*
4 (aerugino): *Pseudomonas aeruginosa*
5 (testost): *Pseudomonas testosteroni*
6 (cepacia): *Pseudomonas cepacia*

| Sequence pair | Homology | Distance | Total positions | Omitted gaps | Unweighted fractions: Match | Mismatch | Gaps |
|---|---|---|---|---|---|---|---|
| Ecoli:ADP | 0.828 | 0.19480 | 1486 | 1 | 0.818 | 0.156 | 0.026 |
| Ecoli:PCA | 0.835 | 0.18622 | 1192 | 1 | 0.827 | 0.153 | 0.020 |
| Ecoli:aerugino | 0.842 | 0.17734 | 1502 | 1 | 0.834 | 0.147 | 0.019 |
| Ecoli:testost | 0.811 | 0.21715 | 1548 | 4 | 0.805 | 0.179 | 0.016 |
| Ecoli:cepacia | 0.814 | 0.21346 | 1460 | 3 | 0.808 | 0.176 | 0.016 |
| ADP:PCA | 0.961 | 0.03964 | 1190 | 1 | 0.952 | 0.029 | 0.019 |
| ADP:aerugino | 0.944 | 0.05774 | 1467 | 0 | 0.939 | 0.049 | 0.012 |
| ADP:testost | 0.808 | 0.22158 | 1478 | 5 | 0.798 | 0.177 | 0.024 |
| ADP:cepacia | 0.827 | 0.19674 | 1456 | 6 | 0.816 | 0.157 | 0.027 |
| PCA:aerugino | 0.934 | 0.06857 | 1185 | 1 | 0.927 | 0.057 | 0.016 |
| PCA:testost | 0.806 | 0.22506 | 1191 | 1 | 0.798 | 0.183 | 0.018 |
| PCA:cepacia | 0.828 | 0.19570 | 1177 | 3 | 0.819 | 0.160 | 0.021 |
| aerugino:testost | 0.822 | 0.20338 | 1493 | 4 | 0.816 | 0.169 | 0.015 |
| aerugino:cepacia | 0.833 | 0.18878 | 1450 | 5 | 0.826 | 0.157 | 0.017 |
| testost:cepacia | 0.886 | 0.12397 | 1453 | 4 | 0.880 | 0.107 | 0.012 |

From the sequence analysis data and the subsequent homology table, we concluded that ADP is not completely identical to either *P. citronellolis* or to *P. aeruginosa*. However, the bacterium is closely related to those two species and is phylogenetically remote from the other analyzed species.

Example 3

Preparation of Atrazine Media

In order to provide a medium for the cultivation of atrazine degrading Pseudomonas (ADP) suitable for use in the present invention, the following components were combined in 1L deionized water: $K_2HPO_4$ (1.6 g); $KH_2PO_4$ (0.4 g); $MgSO_4 \cdot 7H_2O$ (0.2 g); NaCl (0.1 g); $CaCl_2$ (0.02 g); sucrose (1 g); sodium citrate (1 g); atrazine stock solution (1 ml); salt stock solution (20 ml); and vitamin stock solution (20 ml). The salt stock solution contained the following components in 1 L deionized water: EDTA (2.5 g); $ZnSO_4 \cdot 7H_2O$ (11.1 g); $FeSO_4 \cdot 7H_2O$ (5.0 g); $MnSO_4 \cdot H_2O$ (1.54 g); $CuSO_4 \cdot 5H_2O$ (0.4 g); $Co(NO_3)_2 \cdot 6H_2O$ (0.25 g); $Na_2B_4O_7 \cdot 10H_2O$ (0.18 g); and 5.0 mL of concentrated $H_2SO_4$ to retard precipitation of salts. The vitamin stock solution contained the following components in 1L deionized water: thiamin·HCl (5 mg); biotin (2 mg); folic acid (2 mg); nicotinamide (10 mg); and pyridoxine·HCl (10 mg). Atrazine stock solution was prepared by dissolving atrazine (obtained from Chem Service, West Chester, Pa.) in methanol (200 mg/ml), vigorously shaking the solution for several hours, and storing it unfiltered at room temperature in the dark until used. The salt and vitamin stock solutions were filter sterilized and kept at 4° C. The salt solution was added to the media before sterilization. Atrazine was added after sterilization using a sterile pipette. Vitamins were filtered through a 0.2 μm filter again and added to the medium immediately before inoculation with the ADP.

Example 4

Batch Culture of Atrazine Degrading Pseudomonas (ADP)

A batch culture of ADP was prepared in which the bacterium grew at a maximum rate of approximately two hours per generation on the atrazine medium prepared as described in Example 3. The batch culture was grown in a 500 mL Erlenmeyer flask containing 300 mL atrazine medium with shaking at a rate of 100 strokes per minute in a reciprocal shaker at 30° C. in the dark. Cell growth was measured as absorbance at 600 nm using a Beckman DU-70 spectrophotometer (Beckman Instruments, Fullerton, Calif.). Uninoculated medium was used as a blank.

Example 5

Assaying for Atrazine Degradation

Several test methods were used to evaluate the ability of ADP to degrade atrazine. The degradation of atrazine and formation of atrazine metabolites was tested either by HPLC chromatography of the liquid medium, or by counting the radioactivity in the organic phase (ethyl acetate) after liquid-liquid partition. Mineralization (formation of $CO_2$ from the ring carbons) was determined by trapping and counting the evolved carbon dioxide from uniform ring labeled [$^{14}C$] atrazine. In soil experiments atrazine degradation was measured by gas-chromatography after methanol extraction. The exact assay protocol used and the detailed results obtained are given below.

Method A: Atrazine Degradation by a Growing Culture

ADP culture was grown for several days on a solid atrazine medium (2% agar). Using a sterile bacteriological needle, bacteria were transferred to a 100 ppm atrazine medium and grown at 30° C. in an Erlenmeyer flask in the dark without shaking, for 24 hours, or until an $O.D_{600}$ of 0.5 was achieved. The growth medium (10 ml) was inoculated into 300 mL of atrazine medium in a 500 mL Erlenmeyer flask. One bottle was heat killed and served as a control. Atrazine degradation was measured after 24 hours using a high performance liquid chromatography (HPLC) system (Spectra Physics, San Jose, Calif.) consisting of an 8800 pumping system with a Rheodyne 7125 valve-and-loop injector (Cotati, Calif.) fitted with a 20 or 100µL loop and a UVIS-204 detector (Linear Instruments Inc., Reno, Nev.). Absorption at 220 nm was recorded. Analysis of residual atrazine in culture medium was performed using a Spheri-5 $C_{18}$ RP column (Alltech Associates Inc., Deerfield, Ill.) 100 mm in length and 4.6 mm in internal diameter. A reverse phase isocratic HPLC mobile phase was adopted from Vermeulen et al., *J. Chrom.*, 240, 247–253 (1982), which is incorporated herein by reference, except that the isocratic mobile phase contained methanol and 50 mM aqueous ammonium acetate (50:50 v/v). The flow rate was 1 mL/min with the column at room temperature. The chromatograms were displayed on a Spectra Physics Chromjet recording integrator (Spectra Physics, San Jose, Calif.) and captured on a Spectra Physics computer based data analysis system. Authentic standards were chromatographed to aid in the identification of metabolites.

It was found that no atrazine was left in the medium after 24 hours. Furthermore, in a control with heat-killed inoculum, atrazine degradation did not occur.

Method B: Atrazine Degradation by a Non-Growing Culture

Figure 3:
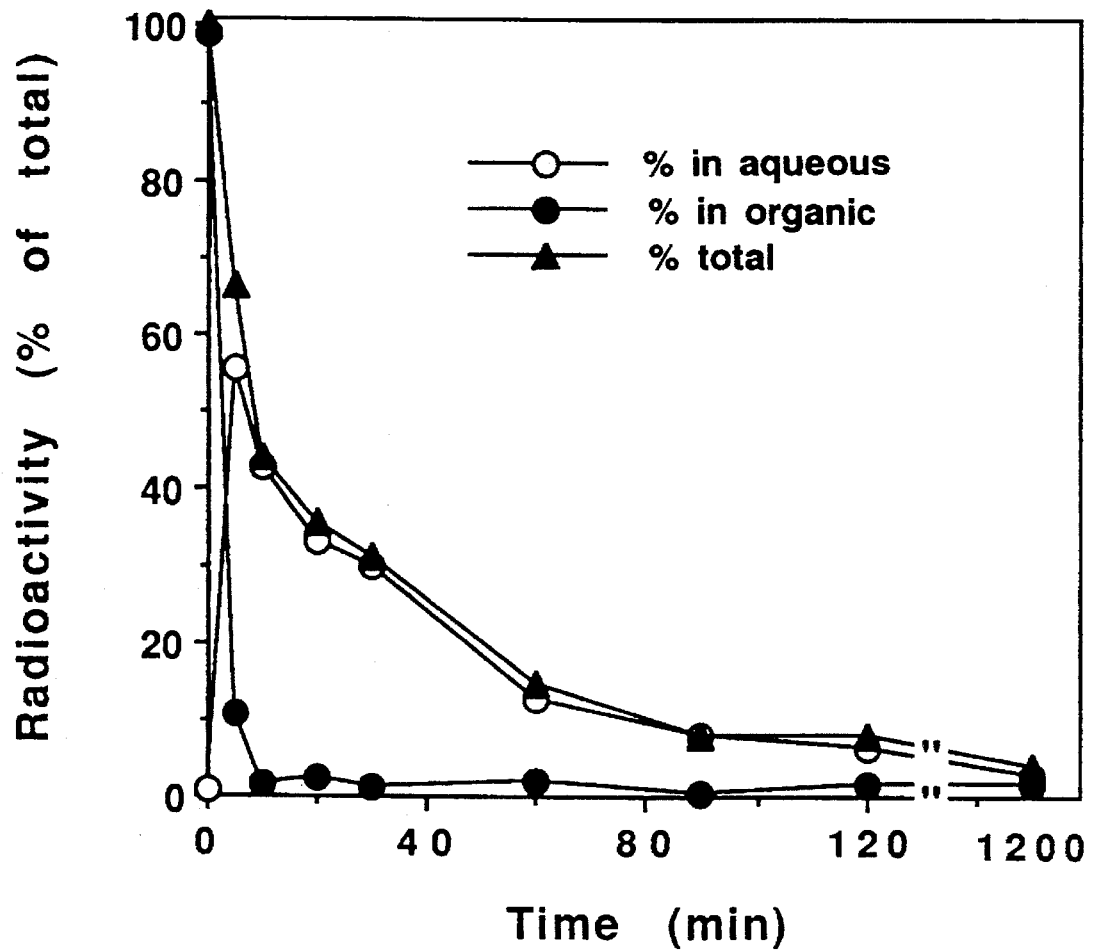
FIG. 3: Degradation of a high concentration of atrazine (2000 ppm) by a cell suspension of atrazine degrading Pseudomonas (ADP).

ADP culture was grown in liquid atrazine medium for 24 hours, or until an $O.D_{600}$ of 0.5 was achieved. The culture was harvested using a centrifuge and washed with a 0.1N phosphate buffer (pH=7.0). Cells were resuspended in the above buffer to yield a concentration having an $O.D_{600}$ of 5.0. The time course of the experiment was started with the amendment of atrazine from a stock solution (200 mg/mL methanol) and from a stock solution of uniformly ring labeled [$^{14}$C]atrazine ($10^4$ dpm/µL) to form a suspension of 2000 ppm and specific activity of about 50,000 dpm/mL medium. At specific times, a 1 mL medium sample was removed and extracted with an equal amount of ethyl acetate. Partitioning was brought to equilibrium by centrifugation at 5000 rpm for 10 minutes. Radioactivity in 100µL samples from each phase was determined with a Beckman LS 6800 scintillation counter (Beckman Instruments, Irvine, Calif.) with channels set to 0–670 and 250–670 for background and sample readings, respectively. The degradation activity of atrazine was measured as disappearance of radioactivity (atrazine) from the ethyl acetate phase and the appearance of transient nonvolatile metabolites in the aqueous phase. The results are given in FIG. 3.

Figure 4:
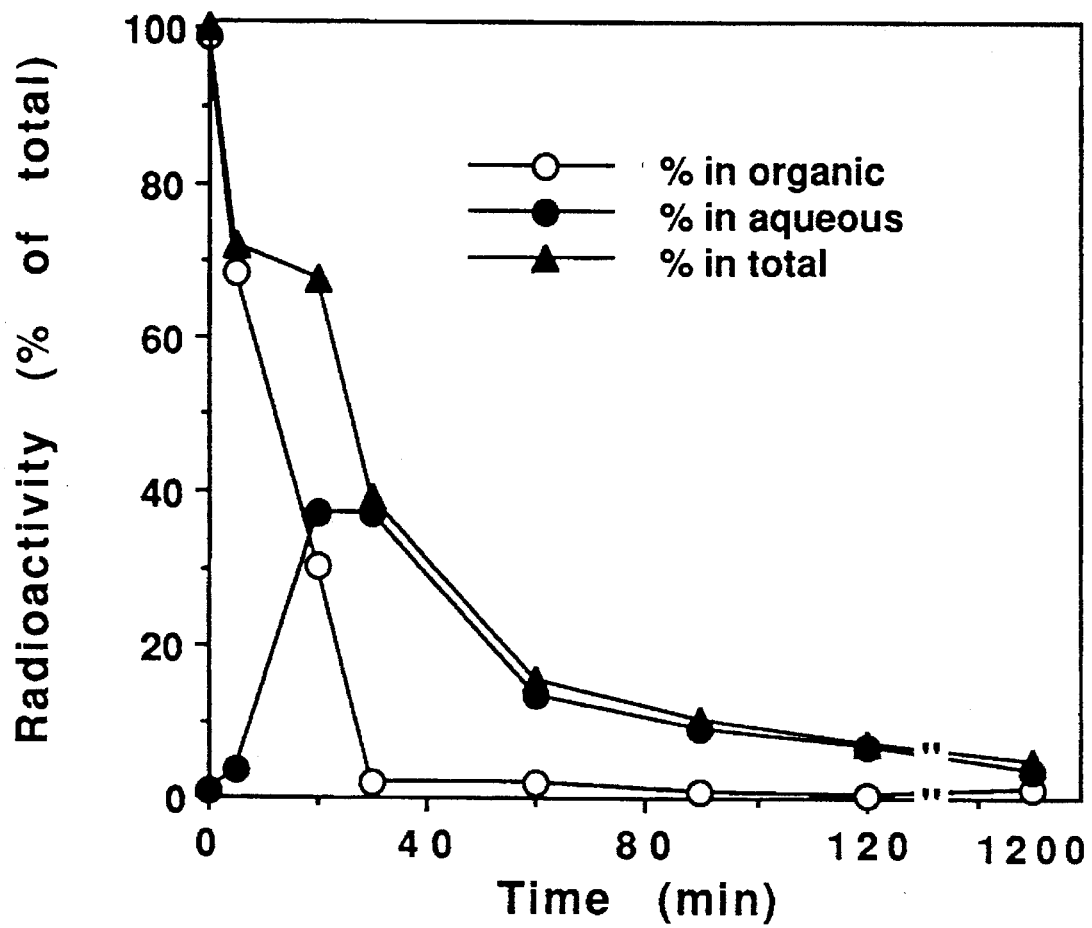
FIG. 4: Degradation of a low concentration of atrazine (200 ppb) by a cell suspension of atrazine degrading Pseudomonas (ADP).

Rapid transformation of atrazine occurred. About 50 minutes after the beginning of the experiment, more than 95% of the radiolabeled atrazine could not be extracted with ethyl acetate. A concomitant formation of transient nonvolatile metabolites was detected in the aqueous phase. Total radioactivity in both phases was calculated from the combined measurements in the aqueous and the organic phases. The missing radioactivity was suspected as disappearance due to mineralization of the radiolabeled ring carbons to form $CO_2$. Two hours after the experiment began, about 90% of the [$^{14}$C]atrazine was apparently mineralized. Similar results were achieved when the initial atrazine concentration was only 200 ppb (FIG. 4). In this experiment only [$^{14}$C] atrazine (specific activity of 7.8 mCi/mmole) was used without the amendment of nonradiolabeled atrazine.

Method C: Atrazine Mineralization by a Non-Growing Culture

Figure 5:
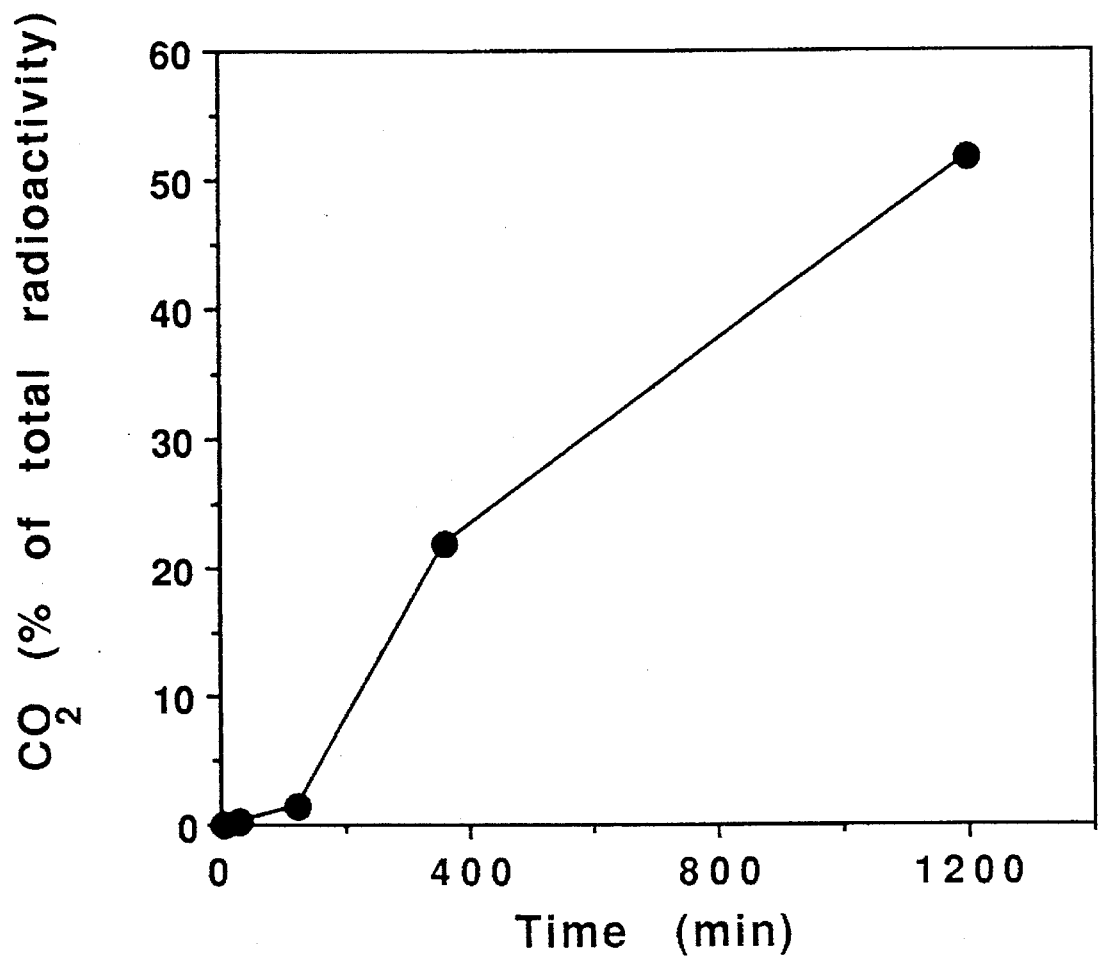
FIG. 5: Mineralization of a high concentration of atrazine (2000 ppm) by a cell suspension of atrazine degrading Pseudomonas (ADP).

Uniformly ring labeled [$^{14}$C]atrazine (7.8 mCi/mmole, 99.6% radiochemically pure; purchased from Sigma® Chemical Co., St. Louis, Mo.) was added to 2000 ppm unlabeled atrazine in 20 mL of sterile atrazine medium to yield $1.1 \times 10^{-3}$ mCi/mL (pH=7.3). The medium was aseptically transferred to a 250 mL biometric Erlenmeyer flask. The assay time course was started with inoculation using a 24-hour old ADP culture (to yield $O.D_{600}=1.0$) and the Erlenmeyer was sealed with an air tight rubber stopper. Incubation was performed at 30° C. with agitation at 25 rpm on a platform shaker. At selected times, the flasks were opened and the amount of $^{14}CO_2$ evolved and trapped in 2 mL of 2N NaOH solution was determined with a Beckman LS 6800 scintillation counter (Beckman Instruments, Irvine, Calif.). An aliquot of the atrazine medium was also analyzed for residual radioactivity. Prior to resealing and further incubation, the NaOH in the trap was replaced with a fresh solution. This experiment demonstrated a degradation of more than 90% of the atrazine in the medium and mineralization of more than 50% of the ring labeled atrazine to form $^{14}CO_2$ in less than 20 hours (FIG. 5).

Method D: Atrazine Degradation in a Petri Dish

Figure 2A:
FIG. 2: Colonies (48-hours old) of an atrazine degrading Pseudomonas (ADP) growing on a solid atrazine medium (500 ppm). The darker area around the colonies is due to the degradation of the atrazine particles in the medium. 2A=a round shape colony. 2B=a C shaped colony. The bar is about 1 cm in length.
Figure 2B:
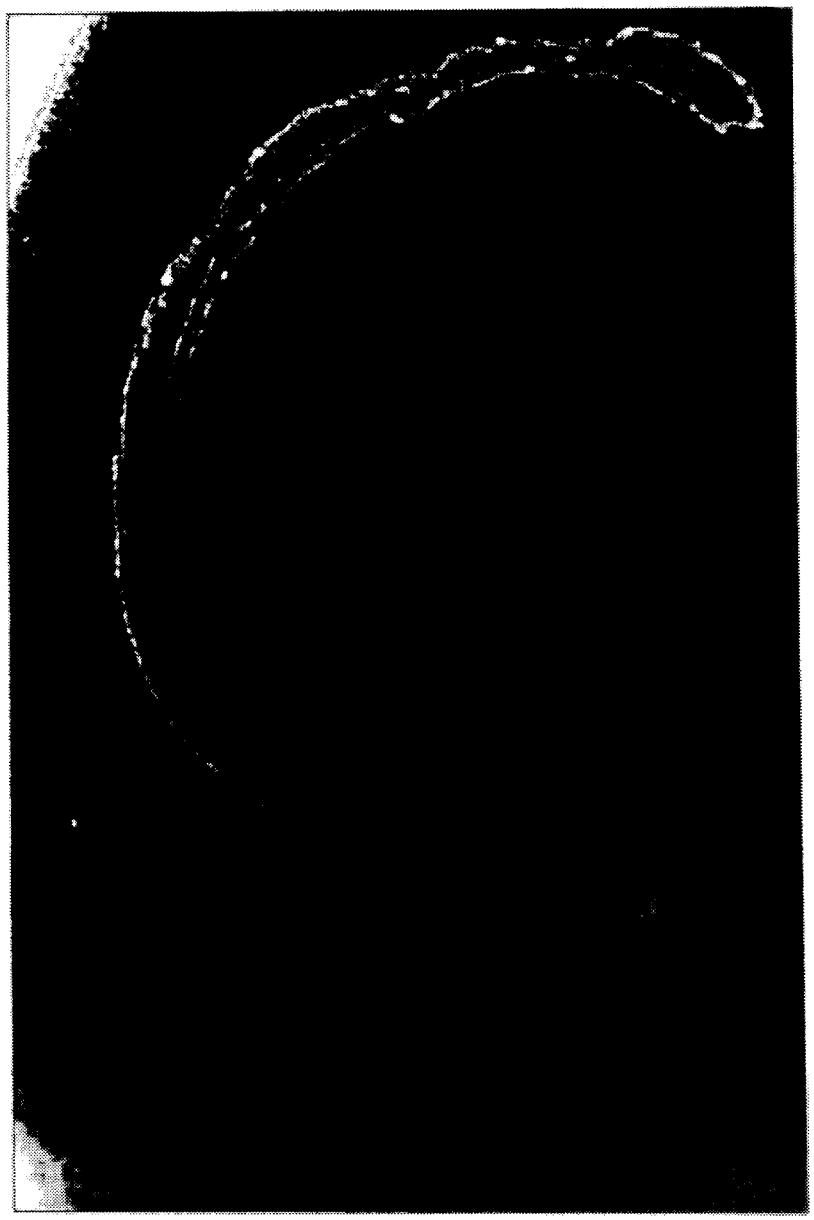

Atrazine (500–1000 ppm) in a solid (2% agar) atrazine medium is visible as an opaque suspension of small particles in the clear agar. When the ADP isolate was grown on such a Petri dish containing high levels of atrazine, it rapidly (within 24 hours) formed a zone of clearing where atrazine was degraded around the ADP colony (FIGS. 2A and 2B).

Example 6

Atrazine Degradation by a Cell-Free Crude Extract

Test 1

A 96-hour old batch culture growing in a 1L Erlenmeyer flask containing 500 mL of atrazine medium at 30° C. was centrifuged at 10,000×g for 30 minutes. The pellet was washed twice with 0.1N phosphate buffer to remove residual atrazine and nutrient from the growth medium and resuspended in the same buffer, to yield a cell concentration having an $O.D_{600}$ of 5.8 and kept on ice. The cold cell suspension was broken by passing it five times through a French press operating at 12,000 PSI. The preparation was then centrifuged for 10 minutes at 10,000×g to remove cell debris, and filtered through a 0.2 µm filter. The resulting preparation contained about 2.5 mg protein per mL. It was immediately subjected to a temperature of −70° C. and frozen.

Figure 6:
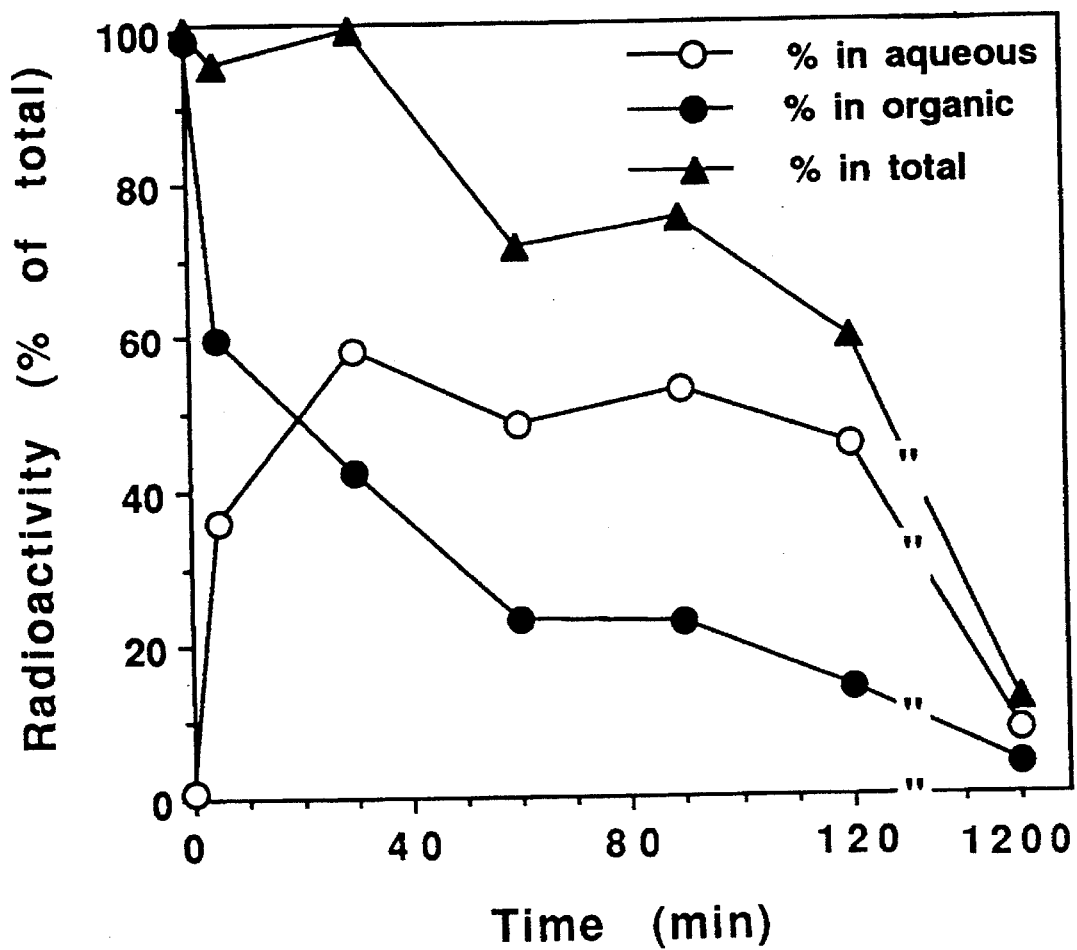
FIG. 6: Degradation of a high concentration of atrazine (2000 ppm) in a crude extract of atrazine degrading Pseudomonas (ADP).

The cell-free extract was diluted with 0.1N phosphate buffer to yield a preparation containing 1 mg protein per mL. This preparation was then warmed to room temperature. The crude cell-free extract (10 mL) was amended with cold atrazine to yield 2000 ppm atrazine, and with [$^{14}$C]atrazine to yield about 12,000 dpm/mL. At selected times, a 1 mL sample was removed and extracted with an equal amount of ethyl acetate. Partitioning was brought to equilibrium by centrifugation at 5,000 rpm for 10 minutes. Radioactivity in 100µL samples from each phase was determined with a Beckman LS 6800 scintillation counter (Beckman Instruments, Irvine, Calif.) with channels set to 0–670 and 250–670 for background and sample readings, respectively. The degradation activity of atrazine was measured as the disappearance of radioactivity (atrazine) from the ethyl acetate phase and the appearance of transient nonvolatile metabolites in the aqueous phase. Rapid degradation of atrazine occurred (FIG. 6). After 5 minutes from the beginning of the experiment, only 60% of the atrazine could be recovered in the organic phase. Transient polar metabolites were formed and peaked at 30 minutes at a level of 60% of the total applied radioactivity. Two hours after the beginning of the experiment, only about 15% of the initial amount of [$^{14}$C]atrazine could be recovered in the organic phase. Twenty hours from the beginning of the experiment less than 15% of the [$^{14}$C]atrazine could be recovered from both phases and was suspected of being mineralized.

Test 2

In a similar experiment, but using only 0.3 mg protein/mL buffer, a 2 mL sample was extracted with ethyl acetate 2 hours after the experiment was begun. A 1 mL sample of each phase was evaporated to near dryness, resuspended in 0.1 mL of methylene chloride and spotted on a thin layer chromatography plate and developed as described below.

Thin layer chromatography (TLC) was performed on silica gel thin layer chromatography precoated plates with a 3 cm preadsorbant spotting layer and a U.V. fluorescent indicator (J.T. Baker Inc., Phillisburg, N.J.) using two solvent systems. The first elution was performed using chloroform, methanol, and formic acid (110:2:2 by volume), the plates were developed up to 17 cm from the bottom of the plate, dried, and eluted a second time in the same solvent system. A third elution was performed with chloroform, methanol, formic acid, and water (75:20:4:2 by volume). Authentic standards of [$^{14}$C]atrazine and hydroxyatrazine (obtained from Ciba Geigy Corp., Greensboro, N.C.) were coeluted. The eluting atrazine and its metabolites were detected using a Berthold TLC-linear analyzer.

Figure 7A:
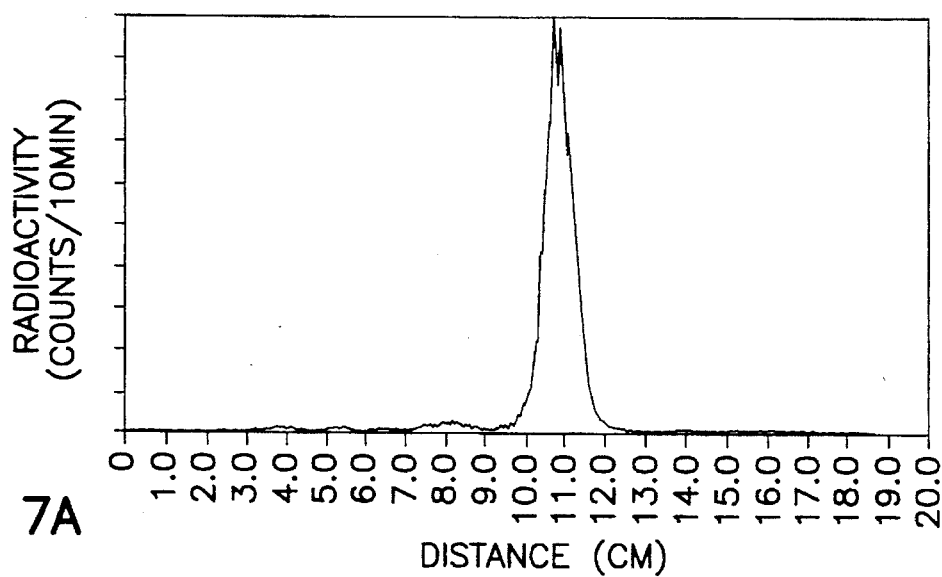
FIG. 7: A radiogram of a thin layer chromatograph (TLC) of [$^{14}$C]atrazine and atrazine degradation products after 2 hours of exposure to cell-free crude extract. Liquid extraction was performed 2 hours after the beginning of the experiment. 7A (ethyl acetate fraction): peak I=simazine; peak II=atrazine. 7B (aqueous fraction eluted in solvent system I): peak I=polar metabolites; peak II= atrazine. 7C (aqueous fraction eluted in solvent system II, which is more polar than solvent system I): peak I=unknown polar metabolites; peak II=hydroxyatrazine; peaks III and IV=unknown metabolites; peak V=atrazine.

It was found that the ethyl acetate phase did not contain any polar metabolites (FIG. 7A) and 92% of the total counts in the organic phase were due to nondegraded atrazine. A contaminant of the [$^{14}$C]atrazine accounted for 3.8% of the counts and was probably simazine (FIG. 7A). About 45% of the total radioactivity left in the medium partitioned into the aqueous phase (FIG. 7B), indicating the presence of polar metabolites which were not eluted using solvent System I. However, using solvent system II it was found that peak 1 in FIG. 7B contained actually at least 4 different metabolites (FIG. 7C). The major metabolite was not identified. It accounted for 72.7% of the total radioactivity in the polar phase. Peak 2 of FIG. 7B coeluted with hydroxyatrazine and accounted for 12.4% of the total radioactivity in the aqueous phase. Two unknown peaks eluted with higher $R_f$ value than hydroxyatrazine and were not identified. Their combined total radioactivity in the aqueous phase was about 8%.

TABLE 4

Mass-Balance of the Radioactivity on the TLC Plate

Figure 7B:
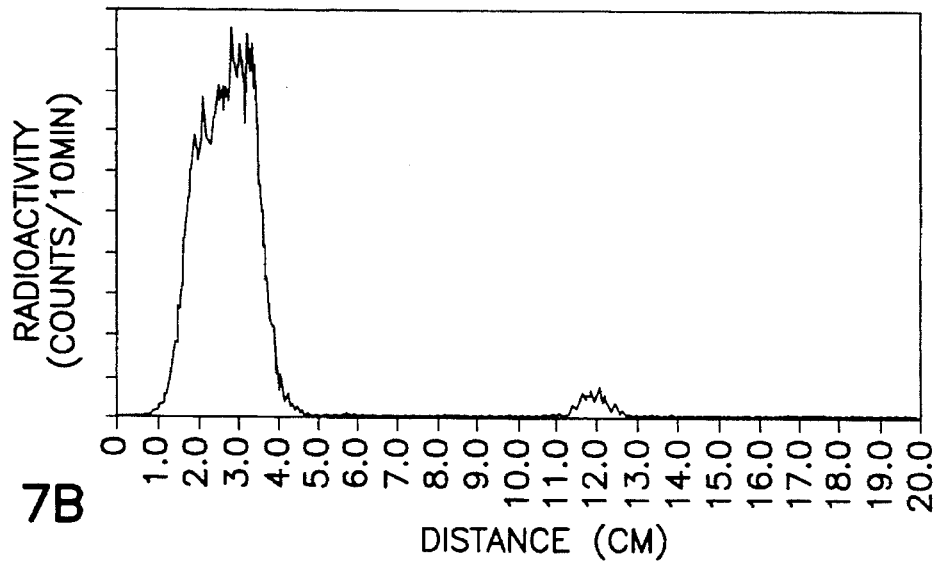
Figure 7C:
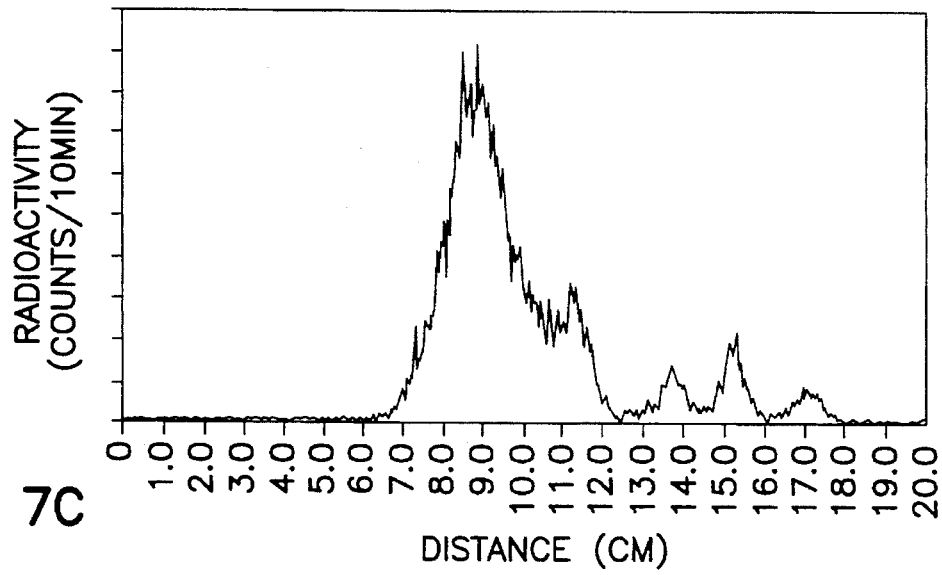

| Peak # | Counts per Peak | Total Counts | % From Total |
|---|---|---|---|
| | FIG. 7A | | |
| 1 | 982 | 26092 | 3.8 |
| 2 | 24062 | 26092 | 92.2 |
| | FIG. 7B | | |
| 1 | 20546 | 22106 | 92.9 |
| 2 | 719 | 22106 | 3.3 |
| | FIG. 7C | | |
| 1 | 17000 | 23369 | 72.7 |
| 2 | 2904 | 23369 | 12.4 |
| 3 | 1092 | 23369 | 4.7 |
| 4 | 1376 | 23369 | 5.9 |

TABLE 4-continued

Mass-Balance of the Radioactivity on the TLC Plate

| Peak # | Counts per Peak | Total Counts | % From Total |
|---|---|---|---|
| 5 | 686 | 23369 | 2.9 |

Test 3

Figure 8:
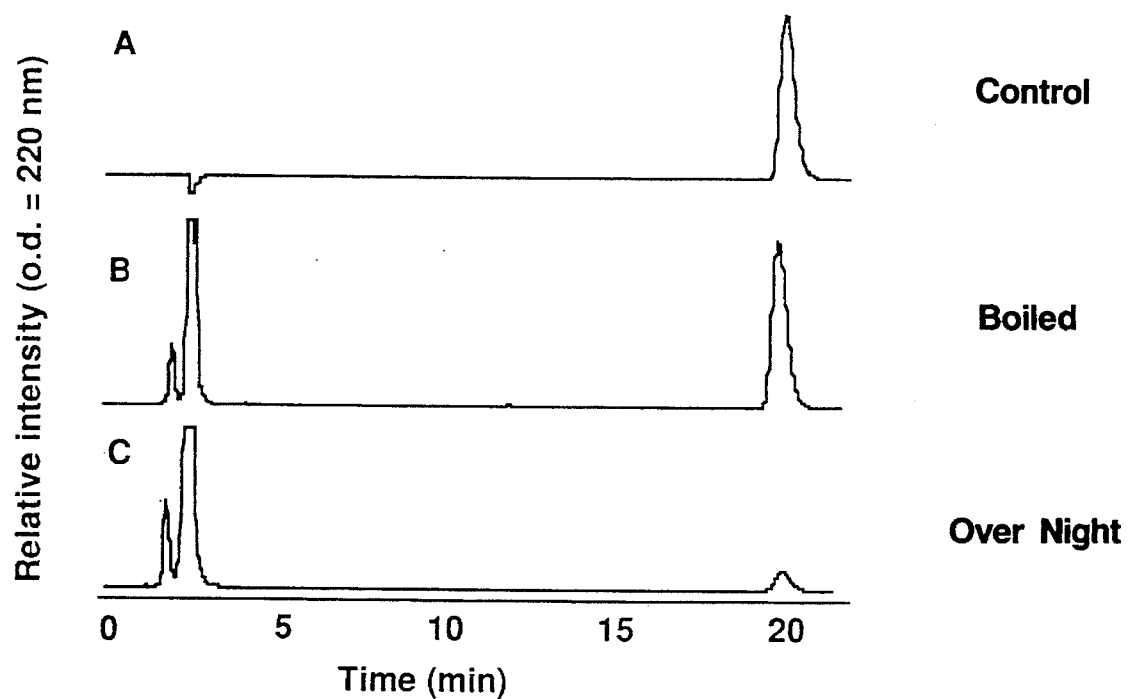
FIG. 8: Atrazine (500 ppm) degradation as measured by high performance liquid chromatography of the incubation medium. The incubation was stopped with trichloroacetic acid and the precipitated proteins were removed by centrifugation. A=Control with no crude extract added. B=Boiled crude extract. C=Control with crude extract.

Atrazine was added to a crude extract (0.5 mg protein per 1 mL of 0.1 N potassium phosphate buffer) to yield 500 ppm. Two control treatments consisted of a boiled (10 minutes) crude extract and of buffer with no crude extract. The experiment was incubated at 30° C. After 18 hours the reaction was brought to termination using 2N TCA (trichloroacetic acid) to precipitate the proteins. The precipitate was removed using a micro-centrifuge (10 minute maximal speed) and a 100µL sample was injected into the HPLC using the same conditions as previously described. Atrazine was not degraded in the heat killed treatment (FIG. 8B) or the control with no crude extract added (FIG. 8A). However, in the crude extract treatment, most of the atrazine was degraded (FIG. 8C). It is interesting to note that no hydroxyatrazine, or dealkylated metabolite were detected in FIG. 8C, probably due to complete turnover of those metabolites. The peaks in the 2–3 minute region represent the TCA that was added to remove the protein and some polar metabolites in the crude extract treatment.

Example 7

Figure 9:
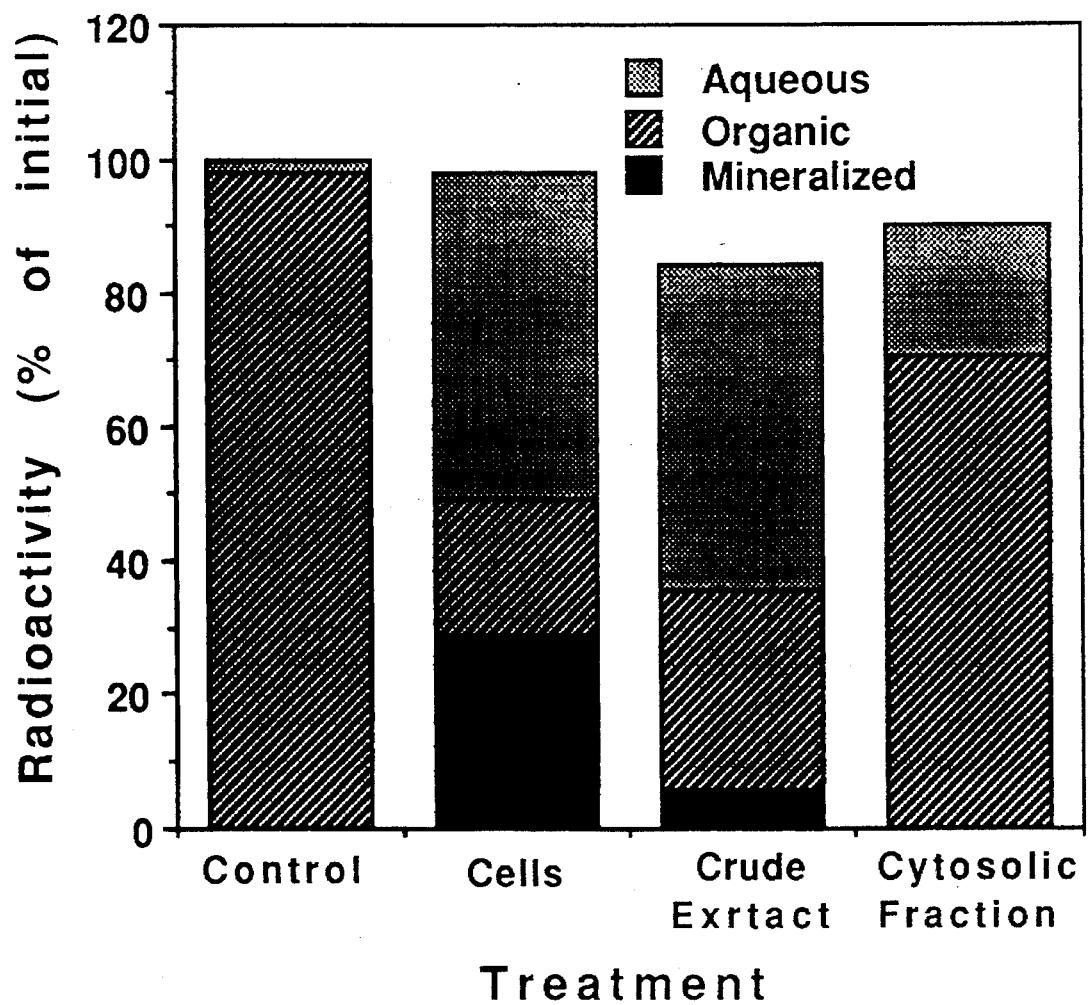
FIG. 9: Recovery of [$^{14}$C]atrazine and metabolites after 1 hour of exposure to cell suspension of atrazine degrading Pseudomonas. The cytosolic fraction was the same as the crude extract except that membrane (and membrane bound proteins) were removed by centrifugation (100,000×g, overnight).

Comparison of Degradation of High Concentration of Atrazine by Cell Suspension and Crude Extracts A culture of ADP was grown for 24 hours on atrazine medium, harvested and washed as previously described. The washed culture was frozen at −20° C. at a concentration having an O.D$_{600}$ of 10.0. An aliquot of the frozen cells was thawed at room temperature, diluted to yield an O.D$_{600}$ of 5.0 with phosphate buffer, French pressed as previously described, and centrifuged at 10,000×g for 30 minutes or at 100,000×g overnight at 4° C. The supernatant of the 10,000×g (crude extract) and the rest of the bacterial suspension were frozen until the overnight centrifugation was completed. Atrazine degradation was assayed in the bacterial suspension (O.D$_{600}$= 5.0 in 0.1N phosphate buffer, pH=7.0), crude extract, and cytosolic fraction (supernatant from 100,000 g centrifugation). A control treatment consisted of buffer with no enzymes or bacteria. A sample (8 mL) of each preparation was transferred to a 20 mL scintillation vial inside a biometric flask (250 mL). The evolved $CO_2$ was trapped in a 2N NaOH trap (2 mL). The experiment was initiated by adding atrazine to the preparations to yield 2,000 ppm (from a stock solution of 200 mg atrazine per mL methanol) and [$^{14}$C]atrazine to yield about 70,000 dpm per mL preparation. The recovery of radioactivity from each fraction (after partition with ethyl acetate) was measured one hour after the experiment began (FIG. 9). The bacterial cells degraded atrazine the fastest. Only 20% of the radioactivity was left in the organic phase and about 30% was mineralized to form $CO_2$. Some mineralization also occurred with the crude extract in which the radioactivity in the aqueous phase accounted for almost 50% of the total recovered activity. The cytosolic fraction was the slowest to degrade atrazine. However, about 20% of the atrazine was recovered as nonvolatile metabolites, indicating that some of the enzymes involved are probably not membrane-bound. No atrazine degradation was detected in the control treatment.

Example 8

ADP Growth on Different N-Sources

Figure 10:
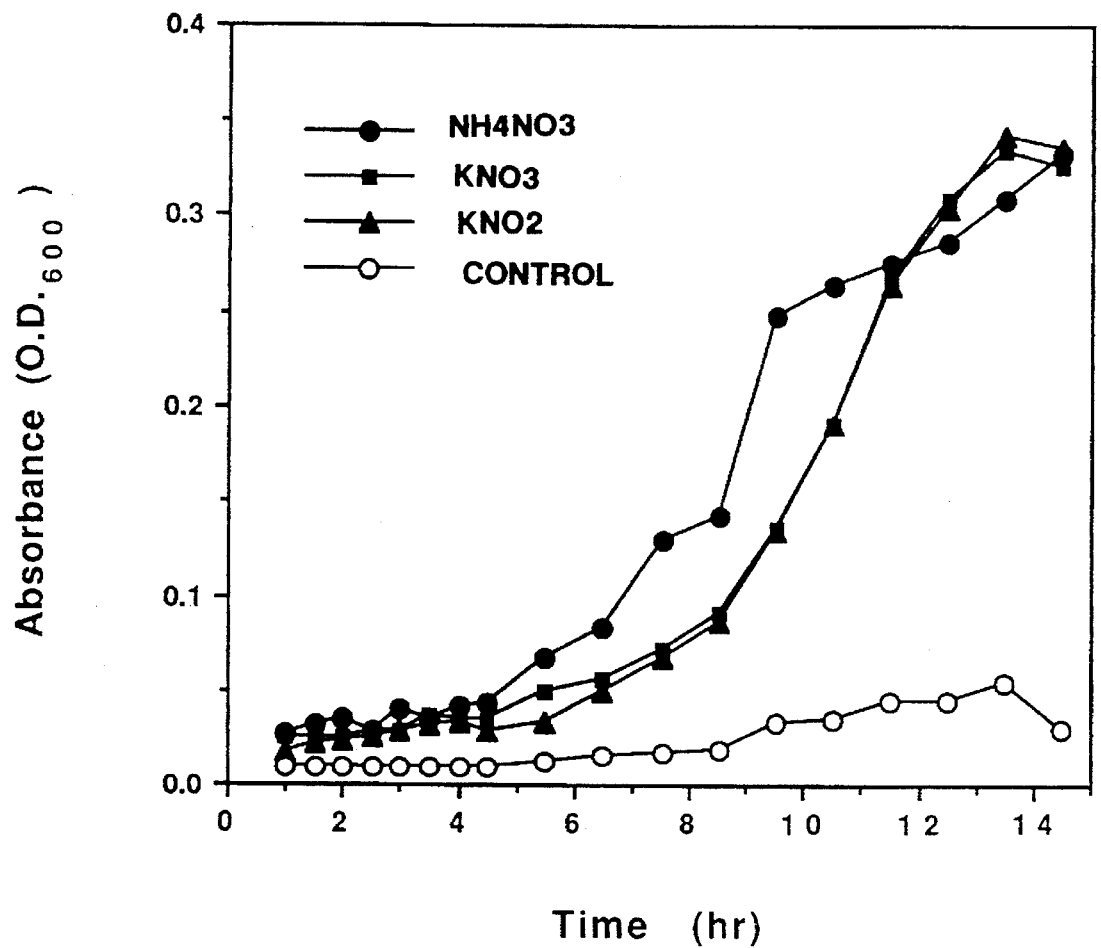
FIG. 10: Growth of atrazine degrading Pseudomonas on different nitrogen sources ($NH_4NO_3$, $KNO_3$, and $KNO_2$).

A medium consisting of similar ingredients as the atrazine medium, but without atrazine, was prepared using various nitrogen sources. The concentration of all nitrogen sources was normalized to equal the amount of nitrogen in 100 ppm atrazine (2.3 mM). To initiate the experiment, a 250 mL flask containing 100 mL medium was inoculated with 3 mL of 24-hour old culture of ADP ($O.D_{600}$=0.3). At specific times, an aliquot was removed and the absorbance at $O.D_{600}$ was measured (FIG. 10). $NH_4NO_3$, $KNO_3$, and $KNO_2$ seem to be equally suitable for use as a nitrogen source to promote the growth of ADP. A slightly quicker growth was observed with $NH_4NO_3$, which might indicate that ammonium ions are a better nitrogen source than is nitrate. Only a slight absorbance increase was observed in the control (no nitrogen source). This absorbance increase was probably due to carry-over of nutrient with the inoculum.

Figure 11:
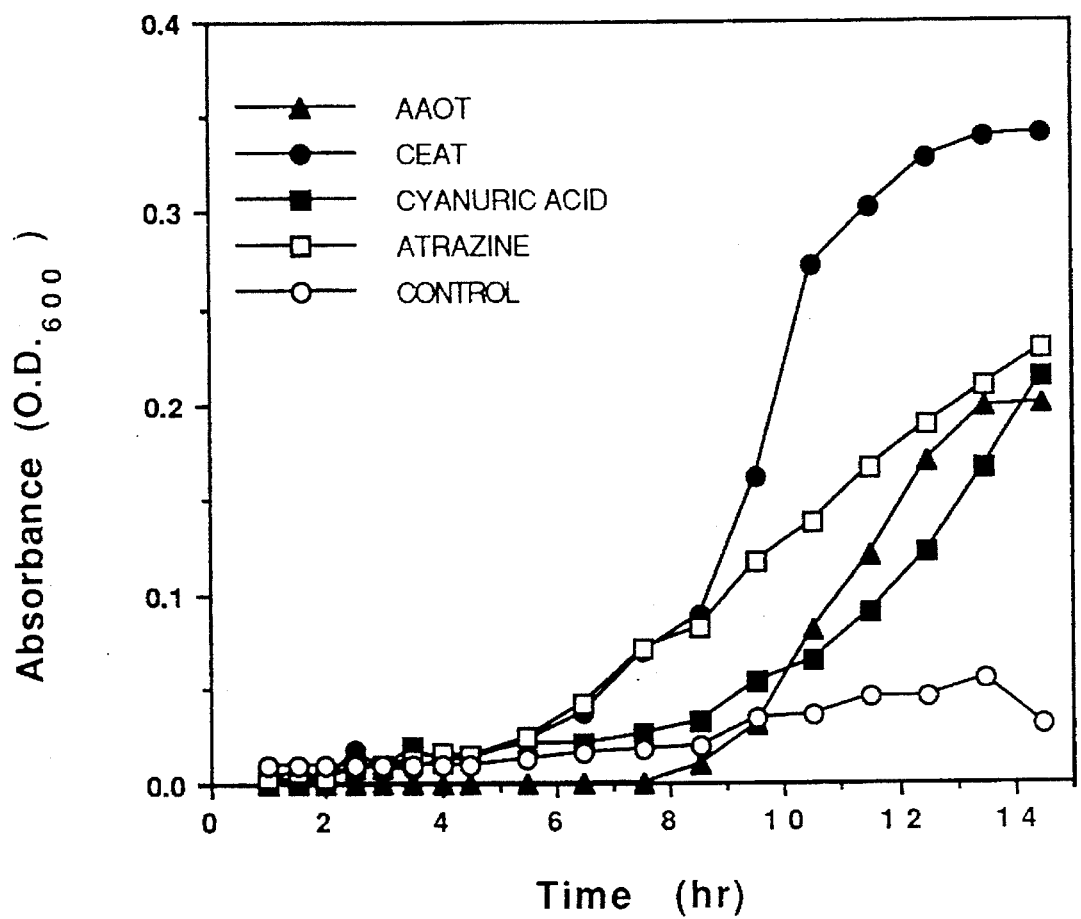
FIG. 11: Growth of atrazine degrading Pseudomonas on atrazine and some atrazine metabolites (AAOT=ammeline, CEAT=desisopropylatrazine).
Figure 12:
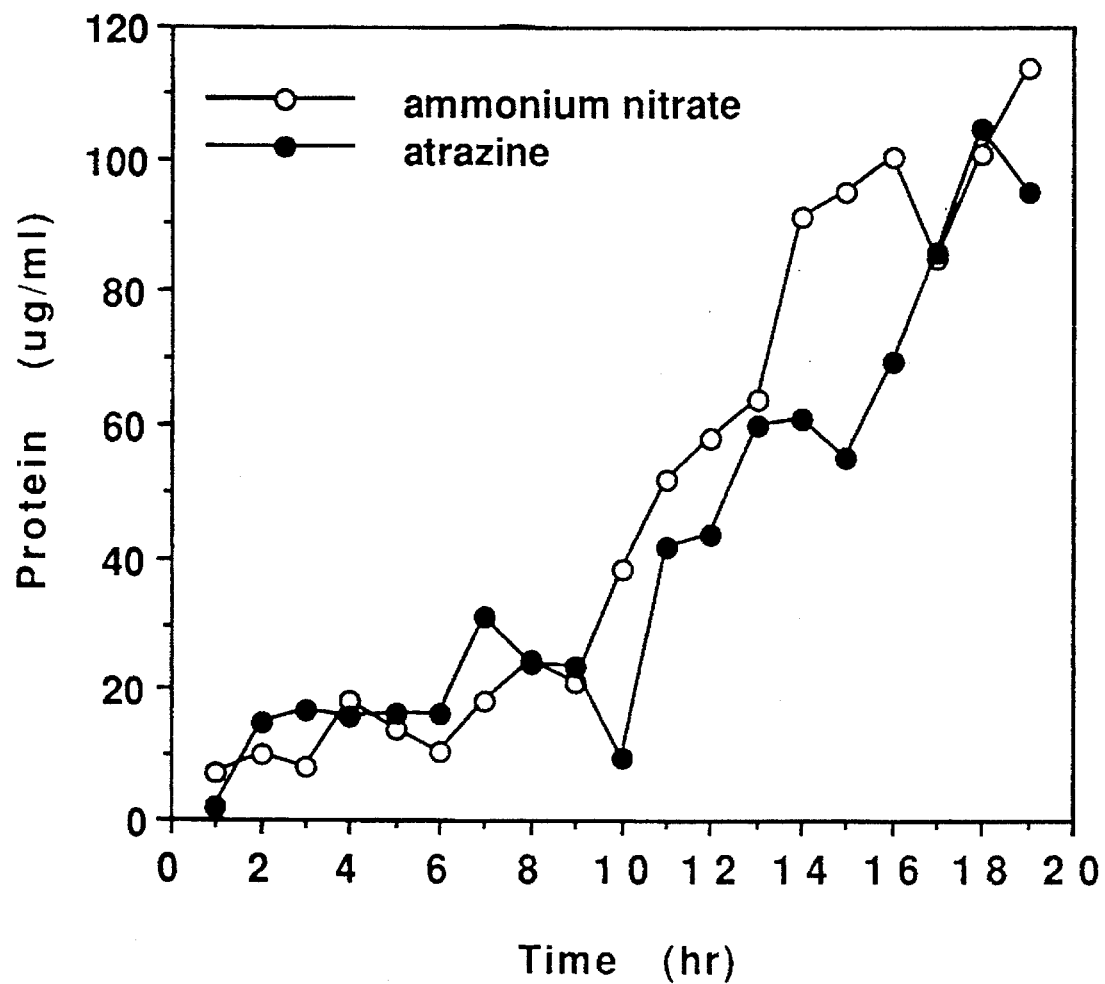
FIG. 12: Growth of atrazine degrading Pseudomonas on atrazine as a nitrogen source as compared to growth using ammonium nitrate as a nitrogen source.

Similarly, atrazine and several of its metabolites were tested for their ability to support growth of ADP being used as the sole nitrogen source (FIG. 11). Doubling time with desisopropylatrazine (obtained from Ciba Geigy Corp.) as a nitrogen source was the quickest (about 80 minutes); however, all the tested metabolites were used by ADP to support growth. In a separate experiment, the growth of ADP on atrazine and ammonium nitrate (both at a concentration equivalent to 2.3 mM nitrogen) was measured as increase in cell protein content (FIG. 12). Both nitrogen sources supported equal growth of the bacterium.

Example 9

Atrazine Degradation in Soil

Agricultural soil (sandy clay) from Madison, Minn., containing a very high concentration of atrazine (up to 40,000 ppm) and aged for several years, was removed from the site and used in a degradation experiment. The soil was air dried. Large soil crumbs were crushed and the soil was sieved through a 2 mm sieve. Soil analysis indicated: total soil carbon 2.7%; organic matter 4.4%; cation exchange capacity (CEC) 31 meq/100 g (dry weight basis); and total nitrogen (TN) 0.24%. The soil was filled into 25L plastic buckets (10L in each). The following treatments were tested: (1) ADP inoculation; (2) sodium citrate amendment without inoculation; and (3) a combination treatment that was inoculated with ADP and amended with sodium citrate. A non-amended treatment served as a control. All treatments were in duplicate. From each duplicate, two soil samples were removed and analyzed for atrazine degradation. Sodium citrate was dissolved in water to yield a solution of 40 g per liter of deionized water. Bacteria were grown as previously reported and suspended in deionized water to yield a concentration having an $O.D_{600}$ of 1.0. To the sodium titrate treatment, 750 mL of sodium citrate solution was amended with 750 mL of deionized water. The inoculated treatment was amended with 750 mL of the bacterial suspension and 750 mL of deionized water. The control was amended with 1.5L of water. All treatments were amended with additional 1.5 L of water. The soil slurries were thoroughly mixed. The plastic buckets were loosely covered with plastic cover to reduce evaporation and incubated in the greenhouse for 48 days. At that time, two soil samples from each bucket (about 70 g soil) were removed for atrazine analysis. The soil samples were immediately frozen and freeze-dried.

Figure 13:
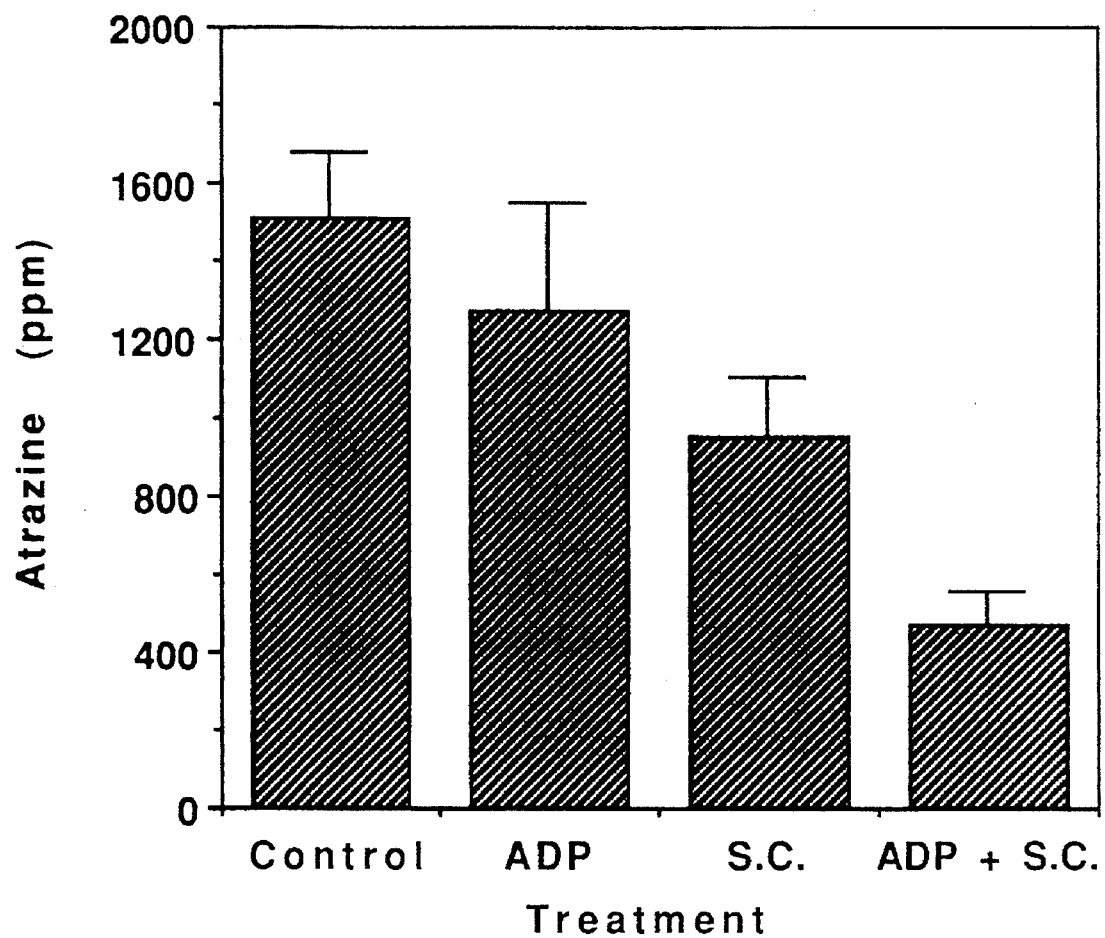
FIG. 13: Atrazine degradation in soil inoculated with atrazine degrading Pseudomonas. S.C.=sodium citrate.

A 10 g sample of freeze dried soil was extracted with 45 mL methanol in a 50 mL disposable polypropylene tube (Corning Inc., Corning, N.Y.). The soil sample was vigorously shaken for 20 seconds and allowed to settle for 24 hours before the methanol was decanted and a second extraction was performed for 2–3 hours. The two methanol extracts were pooled, and centrifuged 5 minutes at 10,000× g. The supernatant fraction was analyzed for atrazine content using a (Hewlett Packard model 5890) gas chromatograph equipped with a flame ionization detector and a DB5 30 m capillary fused silica column (J & W, Folson, Calif.) in a spiteless mode. Each sample was injected in duplicate (1μL). Injector temperature was 250° C., detector temperature was 250° C., and the oven was programmed from 60° C. to 280° C. at a rate of 40° C. per minute and then 5 minutes at 280° C. Atrazine eluted at 7.35 minutes. In the inoculated treatment, 67% of the initial atrazine was degraded in the treatment that was amended with sodium citrate and ADP (FIG. 13). Only 33% of the initial atrazine was degraded when sodium citrate was added without inoculation with ADP, indicating that an indigenous microflora capable of degrading atrazine in the presence of sodium citrate was present in the soil. Inoculation without adding an additional carbon source was not different from the uninoculated, non-amended control.

The complete disclosure of all patents, patent documents, and publications cited herein are incorporated by reference. The foregoing detailed description and examples have been given for clarity of understanding only. No unnecessary limitations are to be understood therefrom. The invention is not limited to the exact details shown and described, the exact details shown and described, for variations obvious to one skilled in the art will be included within the invention defined by the claims.

What is claimed is:

1. A biologically pure culture of a strain of bacteria having all the identifying characteristics of Pseudomonas ATCC No. 55464.

* * * * *

UNITED STATES PATENT AND TRADEMARK OFFICE
CERTIFICATE OF CORRECTION

PATENT NO. : 5,508,193

DATED : April 16th, 1996

INVENTOR(S) : Mandelbaum et al.

It is certified that error appears in the above-identified patent and that said Letters Patent is hereby corrected as shown below:

In column 7, line 11, please delete "August 13, 199" and insert -- August 13, 1993--

Signed and Sealed this

First Day of July, 1997

*Attest:*

*Attesting Officer*

BRUCE LEHMAN

*Commissioner of Patents and Trademarks*